US006495738B1

(12) United States Patent
Folkerts et al.

(10) Patent No.: US 6,495,738 B1
(45) Date of Patent: Dec. 17, 2002

(54) MODIFICATION OF FATTY ACID COMPOSITION IN PLANTS BY EXPRESSION OF A FUNGAL ACYL-COA DESATURASE

(75) Inventors: Otto Folkerts, Guilford, CT (US); Donald J. Merlo, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/280,428

(22) Filed: Mar. 29, 1999

Related U.S. Application Data

(60) Provisional application No. 60/079,840, filed on Mar. 30, 1998.

(51) Int. Cl.$^7$ .......................... A01H 5/00; C12N 15/82
(52) U.S. Cl. .................... 800/281; 800/298; 536/23.2; 435/69.1; 435/468; 435/419
(58) Field of Search .............................. 536/23.2, 23.6; 435/69.1, 468, 419; 800/281, 298

(56) References Cited

U.S. PATENT DOCUMENTS

| 5,057,419 A | 10/1991 | Martin et al. ................ 435/134 |
| 5,614,400 A | 3/1997 | Cahoon et al. .......... 435/172.3 |

FOREIGN PATENT DOCUMENTS

| EP | 0561 569 A2 | 9/1992 |
| EP | 0550 162 A1 | 7/1993 |

OTHER PUBLICATIONS

Van De Loo et al, "An oleate 12–hydroxylase from Ricinus communis L. is a fatty acyl desaturase homolog", Jul. 1995, Proc. Natl. Acad. Sci., vol. 92, pp. 6743–6747.*
Broun et al, "Catalytic Plasticity of Fatty Acid Modification Enzymes Underlying Chemical Diversity of Plant Lipids", Nov. 1998, Science vol. 282, pp. 1315–1317.*
Doerks, "Protein annotation" detective work for function prediction, Jun. 1998, TIG vol. 14 No. 6, pp. 248–250.*
Smith, The challenges of genome sequence annotation or "The devil is in the details", Nov. 1997 Nature Biotechnology vol. 15, pp. 1222–1223.*
Brenner et al, "Errors in genome annotation", Apr. 1999, TIG vol. 15, No. 4, pp. 132–133.*
Bork et al, "Go hunting in sequence databases but watch out for the traps", Oct. 1996, vol. 12 No. 10, pp. 425–427.*
Polashock et al., "Expression of the Yeast Δ–9 Fatty Acid Desaturase in Nicotiana tabacum," Plant Physiol. (1992) 100, 894–901.
Gargano et al., "A Temperature–Sensitive Strain of Histoplasma capsulatum Has an Altered Δ9–Fatty Acid Desaturase Gene," Lipids, vol. 30, No. 10 (1965), 899–906.
Carratu et al., "Membrane lipid perturbation modifies the set point of the temperature of heat shock response in yeast," Proc. Natl. Acad. Sci. USA, vol. 93, pp 3870–3875, Apr. 1996.
Choudhary et al., "Agrobacterium mediated transformation of Petunia hybrida with yeast Δ9 fatty acid desaturase," Plant Growth Regulation 15: 113–116, 1994.
Wang, "Changes of Fatty Acids and Fatty Acid–Derived Flavor Compounds by Expressing the Yeast Δ9 Destaturase Gene in Tomato," J. Agric. Food Chem. 1996, 44, 3399–3402.
Das et al., "Induced Mutation Developing Δ9–Desaturase Defective Unsaturated Fatty Acid Requiring Mutants of Asperigillus nidulans IMI 72731," Indiana Journal of Experimental Biology, vol. 21, Jun. 1983, pp. 339–342.
Tosco et al., "An AP1 Element Is Involved in Transcriptional Regulation of Δ9–Desaturase Gene of Histoplasma capsulatum." Biochemical and Biophysical Research Communications 230, 457–461 (1997).
Chattopadyay et al., "Lipid profiles of conidia of Aspergillus niger and a fatty acid auxotroph," Can. J. Microbiol. vol. 33, 1987, 1116–1120.
Chattopadyay et al., "An unsaturated fatty acid mutant of Aspergillus niger with partially defective Δ9–desaturase" Can. J. Microbiol. vol. 31, 1985, 346–351.
Chattopadyay et al., "Isolation and Characterization of an Unsaturated Fatty Acid Requiring Mutant (UFA4) of Aspergillus niger," Indiana Journal of Experimental Biology, vol. 24, Jul. 1986, pp 421–425.

* cited by examiner

Primary Examiner—Elizabeth McElwain
(74) Attorney, Agent, or Firm—Donald R. Stuart; Kenneth B. Ludwig

(57) ABSTRACT

Genes-encoding a delta-9 CoA desaturase from *Aspergillus nidulans* have been isolated. The proteins encoded by genes, when expressed in a plant, can alter the saturate levels of the oil.

13 Claims, No Drawings

SEQUENCE LISTING

<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:5' primer

<400> SEQUENCE: 1
cayaayayyc aycaygartt ycc                                              23

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:3' primer
<223> OTHER INFORMATION: n can be a, g, c, or t

<400> SEQUENCE: 2
ttyttnarrt crtangc                                                     17

<210> SEQ ID NO 3
<211> LENGTH: 118
<212> TYPE: DNA
<213> ORGANISM: Zea mays
<220> FEATURE:
<221> NAME/KEY: CDS
<222> LOCATION: (3)..(116)

<400> SEQUENCE: 3 ac ttt cat cac gag ttc ccc tcg gac tac cgt aac gcc atc gaa tgg         47
   Phe His His Glu Phe Pro Ser Asp Tyr Arg Asn Ala Ile Glu Trp
    1               5                  10                  15 cac cag tat gat ccc acc aag tgg tcc atc tgg gcc tgg aag cag ctt        95
His Gln Tyr Asp Pro Thr Lys Trp Ser Ile Trp Ala Trp Lys Gln Leu
             20                  25                  30 ggt ctt gcc tac gac ctt aaa aa                                         118
Gly Leu Ala Tyr Asp Leu Lys
             35

<210> SEQ ID NO 4
<211> LENGTH: 38
<212> TYPE: PRT
<213> ORGANISM: Zea mays

<400> SEQUENCE: 4

Phe His His Glu Phe Pro Ser Asp Tyr Arg Asn Ala Ile Glu Trp His
 1               5                  10                  15
Gln Tyr Asp Pro Thr Lys Trp Ser Ile Trp Ala Trp Lys Gln Leu Gly
             20                  25                  30
Leu Ala Tyr Asp Leu Lys
             35

<210> SEQ ID NO 5
<211> LENGTH: 1589
<212> TYPE: DNA
<213> ORGANISM: Aspergillus nidulans
<220> FEATURE:
<221> NAME/KEY: CDS
<222> LOCATION: (4)..(1368)

<400> SEQUENCE: 5 gcc atg tct gca cca acg gcg gac atc agg gct cgc gcc ccg gag gcc        48

```
        Met Ser Ala Pro Thr Ala Asp Ile Arg Ala Arg Ala Pro Glu Ala
         1               5                  10                 15 aaa aag gtt cac atc gct gac act gct atc aac cgc cat aac tgg tac      96
Lys Lys Val His Ile Ala Asp Thr Ala Ile Asn Arg His Asn Trp Tyr
                 20                  25                  30 aag cat gtg aac tgg ctg aac gtt ttc ctg atc atc ggt atc ccg ctt     144
Lys His Val Asn Trp Leu Asn Val Phe Leu Ile Ile Gly Ile Pro Leu
             35                  40                  45 tat ggg tgc att cag gcg ttc tgg gtg cca ctg cag ctg aag act gcc     192
Tyr Gly Cys Ile Gln Ala Phe Trp Val Pro Leu Gln Leu Lys Thr Ala
         50                  55                  60 atc tgg gcc gtc atc tac tac ttt ttc acc ggt ctc ggt atc aca gca     240
Ile Trp Ala Val Ile Tyr Tyr Phe Phe Thr Gly Leu Gly Ile Thr Ala
     65                  70                  75 ggt tac cat cgt cta tgg gct cac tgc tcg tac tcc gcc acc ctt cct     288
Gly Tyr His Arg Leu Trp Ala His Cys Ser Tyr Ser Ala Thr Leu Pro
 80                  85                  90                  95 ttg cgt atc tgg ctc gct gcc gtt ggt ggt ggt gcc gtc gaa ggt tct     336
Leu Arg Ile Trp Leu Ala Ala Val Gly Gly Gly Ala Val Glu Gly Ser
                100                 105                 110 atc cgc tgg tgg gct cgt gac cac cgc gct cac cac cgc tac acc gat     384
Ile Arg Trp Trp Ala Arg Asp His Arg Ala His His Arg Tyr Thr Asp
            115                 120                 125 acc gac aaa gac ccg tac tcc gtt cgc aag ggt ctg ctc tac tct cac     432
Thr Asp Lys Asp Pro Tyr Ser Val Arg Lys Gly Leu Leu Tyr Ser His
        130                 135                 140 ctt ggc tgg atg gtg atg aag cag aac cct aag cgt att ggc cgt acc     480
Leu Gly Trp Met Val Met Lys Gln Asn Pro Lys Arg Ile Gly Arg Thr
    145                 150                 155 gat att tcc gac ctg aac gag gac ccc gtc gtt gtc tgg cag cac cgc     528
Asp Ile Ser Asp Leu Asn Glu Asp Pro Val Val Val Trp Gln His Arg
160                 165                 170                 175 aac tac ctc aag gtc gtt ttc acg atg gga ttg gct gtg cct atg ctt     576
Asn Tyr Leu Lys Val Val Phe Thr Met Gly Leu Ala Val Pro Met Leu
                180                 185                 190 gtt gct ggt ctt gga tgg ggt gac tgg ttg ggc ggc ttc gtg tat gcc     624
Val Ala Gly Leu Gly Trp Gly Asp Trp Leu Gly Gly Phe Val Tyr Ala
            195                 200                 205 ggc att ctg cgt atc ttc ttc gtc cag cag gcg act ttc tgc gtc aac     672
Gly Ile Leu Arg Ile Phe Phe Val Gln Gln Ala Thr Phe Cys Val Asn
        210                 215                 220 tct ttg gcc cac tgg ctc ggt gac cag ccc ttc gat gac cgc aac tca     720
Ser Leu Ala His Trp Leu Gly Asp Gln Pro Phe Asp Asp Arg Asn Ser
    225                 230                 235 cct cgt gac cac gtt atc acc gct ctc gtc acc ctt gga gag ggc tac     768
Pro Arg Asp His Val Ile Thr Ala Leu Val Thr Leu Gly Glu Gly Tyr
240                 245                 250                 255 cac aac ttc cac cac gag ttc ccc tcg gac tac cgt aac gcc atc gaa     816
His Asn Phe His His Glu Phe Pro Ser Asp Tyr Arg Asn Ala Ile Glu
                260                 265                 270 tgg cac cag tat gat ccc acc aag tgg tcc atc tgg gcc tgg aag cag     864
Trp His Gln Tyr Asp Pro Thr Lys Trp Ser Ile Trp Ala Trp Lys Gln
            275                 280                 285 ctt ggt ctt gcc tac gac ctg aag aag ttc cgt gcc aac gag att gag     912
Leu Gly Leu Ala Tyr Asp Leu Lys Lys Phe Arg Ala Asn Glu Ile Glu
        290                 295                 300 aag ggt cgt gtc cag cag ctc cag aag aag ctt gac cgt aag cgt gcc     960
Lys Gly Arg Val Gln Gln Leu Gln Lys Lys Leu Asp Arg Lys Arg Ala
305                 310                 315
```

```
act ctc gat tgg ggt act cct ctt gac cag ctc ccc gtc atg gag tgg    1008
Thr Leu Asp Trp Gly Thr Pro Leu Asp Gln Leu Pro Val Met Glu Trp
320                 325                 330                 335 gac gac tac gtc gag cag gct aag aac ggc cgc ggt ctc gtg gct att    1056
Asp Asp Tyr Val Glu Gln Ala Lys Asn Gly Arg Gly Leu Val Ala Ile
                340                 345                 350 gcc ggt gtt gtc cac gat gtc acg gac ttc atc aaa gac cac ccc ggt    1104
Ala Gly Val Val His Asp Val Thr Asp Phe Ile Lys Asp His Pro Gly
            355                 360                 365 ggc aag gcc atg atc agc tcc ggt att ggg aag gac gcc acc gcc atg    1152
Gly Lys Ala Met Ile Ser Ser Gly Ile Gly Lys Asp Ala Thr Ala Met
        370                 375                 380 ttc aac ggt ggt gtc tac tac cac tcc aac gcc gca cac aac ctc ctc    1200
Phe Asn Gly Gly Val Tyr Tyr His Ser Asn Ala Ala His Asn Leu Leu
    385                 390                 395 tct acc atg cgt gtt ggt gtt atc cgc ggc ggc tgt gaa gtc gaa atc    1248
Ser Thr Met Arg Val Gly Val Ile Arg Gly Gly Cys Glu Val Glu Ile
400                 405                 410                 415 tgg aag cgt gcc cag aag gag aac gtg gag tac gtg cgt gat ggc tct    1296
Trp Lys Arg Ala Gln Lys Glu Asn Val Glu Tyr Val Arg Asp Gly Ser
                420                 425                 430 ggc cag cgc gtc atc cgt gcc ggc gag cag cca acc aag atc cca gaa    1344
Gly Gln Arg Val Ile Arg Ala Gly Glu Gln Pro Thr Lys Ile Pro Glu
            435                 440                 445 ccc att ccc aca gcg gat gcg gcg tgatctgttt ttttttttgt ttcccgctcc   1398
Pro Ile Pro Thr Ala Asp Ala Ala
        450                 455 acattgtccc actttagggt ctgaaactta gcacactggc gtttgatcgt tccttagagt   1458
ttggagttgc ggagttttgg tccatgtctg tcggtgtagt ctacccatgt tgatccgtct   1518
acctaaaagc gagacttgaa atgagatatg ccatcaactt acaatttgaa aacaaaaaaa   1578 aaaaaaaaa a                                                         1589
```

<210> SEQ ID NO 6
<211> LENGTH: 455
<212> TYPE: PRT
<213> ORGANISM: Aspergillus nidulans

<400> SEQUENCE: 6

```
Met Ser Ala Pro Thr Ala Asp Ile Arg Ala Arg Ala Pro Glu Ala Lys
  1               5                  10                  15

Lys Val His Ile Ala Asp Thr Ala Ile Asn Arg His Asn Trp Tyr Lys
                 20                  25                  30

His Val Asn Trp Leu Asn Val Phe Leu Ile Ile Gly Ile Pro Leu Tyr
             35                  40                  45

Gly Cys Ile Gln Ala Phe Trp Val Pro Leu Gln Leu Lys Thr Ala Ile
         50                  55                  60

Trp Ala Val Ile Tyr Tyr Phe Thr Gly Leu Gly Ile Thr Ala Gly
 65                  70                  75                  80

Tyr His Arg Leu Trp Ala His Cys Ser Tyr Ser Ala Thr Leu Pro Leu
                 85                  90                  95

Arg Ile Trp Leu Ala Val Gly Gly Gly Ala Val Glu Gly Ser Ile
            100                 105                 110

Arg Trp Trp Ala Arg Asp His Arg Ala His His Arg Tyr Thr Asp Thr
        115                 120                 125

Asp Lys Asp Pro Tyr Ser Val Arg Lys Gly Leu Leu Tyr Ser His Leu
    130                 135                 140
```

```
Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
                180                 185                 190

Ala Gly Leu Gly Trp Gly Asp Trp Leu Gly Phe Val Tyr Ala Gly
            195                 200                 205

Ile Leu Arg Ile Phe Phe Val Gln Gln Ala Thr Phe Cys Val Asn Ser
210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
                260                 265                 270

His Gln Tyr Asp Pro Thr Lys Trp Ser Ile Trp Ala Trp Lys Gln Leu
                275                 280                 285

Gly Leu Ala Tyr Asp Leu Lys Lys Phe Arg Ala Asn Glu Ile Glu Lys
290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
                340                 345                 350

Gly Val Val His Asp Val Thr Asp Phe Ile Lys Asp His Pro Gly Gly
                355                 360                 365

Lys Ala Met Ile Ser Ser Gly Ile Gly Lys Asp Ala Thr Ala Met Phe
370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
                420                 425                 430

Gln Arg Val Ile Arg Ala Gly Glu Gln Pro Thr Lys Ile Pro Glu Pro
                435                 440                 445

Ile Pro Thr Ala Asp Ala Ala
    450                 455

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence:primer

<400> SEQUENCE: 7
ggtacggcca tattggccac catggcacca acggcggaca tcagggct                    48

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:primer
```

<400> SEQUENCE: 8

```
atatcggcca gagaggcctc acgccgcatc cgctgtggga atggg          45
```

<210> SEQ ID NO 9
<211> LENGTH: 1267
<212> TYPE: DNA
<213> ORGANISM: Artificial Sequence
<220> FEATURE:
<223> OTHER INFORMATION: Description of Artificial Sequence: portion of pGGN62-2

<400> SEQUENCE: 9

```
ttttctagaa agcttgccga gtgccatcct tggacactcg ataaagtata ttttattttt    60
tttattttgc caaccaaact ttttgtggta tgttcctaca ctatgtagat ctacatgtac   120
cattttggca caattacaaa aatgttttct ataactatta gatttagttc gtttatttga   180
atttcttcgg aaaattcaca tatgaactgc aagtcactcg aaacatgaaa aaccgtgcat   240
gcaaaataaa tgatatgcat gttatctagc acaagttacg accgatttca gaagcagacc   300
agaatcttca agcaccatgc tcactaaaca tgaccgtgaa cttgttatcc agttgtttaa   360
aaattgtata aaacacaaat aaagtcagaa attaatgaaa cttgtccaca tgtcatgata   420
tcatatatag aggttgtgat aaaaatttga tattgtttcg gtaaagttgt gacgtactat   480
gtgtagaaac ctaagtgacc tacacataaa atcatagagt ttcaatgtag ttcactcgac   540
aaagactttg tcaagtgtcc gataaaaagt attcagcaaa gaagccgttg tcgatttact   600
gttcgtcgag atctctttgc cgagtgtcac actaggcaaa gtctttacgg agtgttttc   660
aggcttttgac actcggcaaa gcgctcgatt ccagtagtga cagtaatttg catcaaaaat   720
agccgagaga tttaaaatga gtcaactaat agaccaacta attattagct attagtcgtt   780
agcttcttta atctaagcta aaaccaacta atagcttatt tgttgaatta caattagctc   840
aacggaattc tctgtttttt ctataaaaaa gggaaactgc ccctcattta cagcaaactg   900
tccgctgcct gtcgtccaga tacaatgaac gtacctagta ggaactcttt tacacgctcg   960
gtcgctcgcc gcggatcgga gtcccaggaa cacgacacca ctgtggaaca cgacaaagtc  1020
tgctcagagg cggccacacc ctggcgtgca ccgagccgga gcccggataa gcacggtaag  1080
gagagtacgg cgggacgtgg cgacccgtgt gtctgctgcc acgcagcctt cctccacgta  1140
gccgcgcggc cgcgccacgt accagggccc ggcgctggta taaatgcgcg ccacctccgc  1200
tttagttctg catacagcca acccaacaca cacccgagca tatcacagtg acactacacc  1260
atggaaa                                                            1267
```

<210> SEQ ID NO 10
<211> LENGTH: 1547
<212> TYPE: DNA
<213> ORGANISM: Phaseolus vulgaris

<400> SEQUENCE: 10

```
gaattccatt gtactcccag tatcattata gtgaaagttt tggctctctc gccggtggtt    60
ttttacctct atttaaaggg gtttttccacc taaaaattct ggtatcattc tcactttact   120
tgttacttta atttctcata atctttggtt gaaattatca cgcttccgca cacgatatcc   180
ctacaaattt attatttgtt aaacattttc aaaccgcata aattttatg aagtcccgtc   240
tatctttaat gtagtctaac attttcatat tgaaatatat aatttactta attttagcgt   300
tggtagaaag cataaagatt tattcttatt cttcttcata taaatgttta atatacaata   360
```

```
taaacaaatt ctttacctta agaaggattt cccattttat attttaaaaa tatatttatc    420
aaatattttt caaccacgta aatctcataa taataagttg tttcaaaagt aataaaattt    480
aactccataa ttttttttatt cgactgatct taaagcaaca cccagtgaca caactagcca   540 ttttttttctt tgaataaaaa aatccaatta tcattgtatt ttttttatac aatgaaaatt   600
tcaccaaaca atcatttgtg gtatttctga agcaagtcat gttatgcaaa attctataat   660
tcccatttga cactacggaa gtaactgaag atctgctttt acatgcgaga cacatcttct    720
aaagtaattt taataatagt tactatattc aagatttcat atatcaaata ctcaatatta   780
cttctaaaaa attaattaga tataattaaa atattacttt tttaattttta agtttaattg   840 ttgaatttgt gactattgat ttattattct actatgttta aattgttttta tagatagttt   900 aaagtaaata taagtaatgt agtagagtgt tagagtgtta ccctaaaccaa taaactataa   960 gatttatggt ggactaattt tcatatattt cttattgctt ttaccttttc ttggtatgta  1020
agtccgtaac tagaattaca gtgggttgtc atggcactct gtggtctttt ggttcatgca  1080
tgggtcttgc gcaagaaaaa gacaaagaac aagaaaaaa gacaaaacag agagacaaaa   1140
cgcaatcaca caaccaactc aaattagtca ctggctgatc aagatcgccg cgtccatgta  1200
tgtctaaatg ccatgcaaag caacacgtgc ttaacatgca cttttaaatgg ctcacccatc  1260 tcaacccaca cacaaacaca ttgcctttttt cttcatcatc accacaacca cctgtatata  1320
ttcattctct tccgccacct caatttcttc acttcaacac acgtcaacct gcatatgcgt  1380
gtcatcccat gcccaaatct ccatgcatgt tccaaccacc ttctctctta tataatacct  1440
ataaatacct ctaatatcac tcacttcttt catcatccat ccatccagag tactactact  1500
ctactactat aatacccccaa cccaactcat attcaatact actctac             1547

<210> SEQ ID NO 11
<211> LENGTH: 10323
<212> TYPE: DNA
<213> ORGANISM: Artificial Sequence
<220> FEATURE:
<223> OTHER INFORMATION: Description of Artificial Sequence:pDAB1542

<400> SEQUENCE: 11
aagcttgctt ggtcgttccg cgtgaacgtc ggctcgattg tacctgcgtt caaatacttt    60
gcgatcgtgt tgcgcgcctg cccggtgcgt cggctgatct cacggatcga ctgcttctct  120
cgcaacgcca tccgacggat gatgtttaaa agtcccatgt ggatcactcc gttgccccgt  180
cgctcaccgt gttgggggga agtgcacat ggctcagttc tcaatggaaa ttatctgcct   240
aaccggctca gttctgcgta gaaaccaaca tgcaagctcc accgggtgca aagcggcagc   300
ggcggcagga tatattcaat tgtaaatggc ttcatgtccg ggaaatctac atggatcagc   360
aatgagtatg atggtcaata tggagaaaaa gaaagagtaa ttaccaattt tttttcaatt   420
caaaaatgta gatgtccgca gcgttattat aaaatgaaag tacattttga taaacgaca   480 aattacgatc cgtcgtatttt ataggcgaaa gcaataaaca aattattcta attcggaaat   540
ctttatttcg acgtgtctac attcacgtcc aaatggggga gatccgtcga cctgcagtga   600
ggtctgcctc gtgaagaagg tgttgctgac tcataccagg cctgaatcgc ccatcatcc    660 agccagaaag tgagggagcc acggttgatg agagctttgt tgtaggtgga ccagttggtg   720
attttgaact tttgctttgc cacggaacgg tctgcgttgt cgggaagatg cgtgatctga   780
tccttcaact cagcaaaagt tcgatttatt caacaaagcc acgttgtgtc tcaaaatctc   840
```

-continued

| | | | |
|---|---|---|---|
| tgatgttaca | ttgcacaaga | taaaaatata tcatcatgaa caataaaact gtctgcttac | 900 |
| ataaacagta | atacaagggg | tgttatgagc catattcaac gggaaacgtc ttgctcgagg | 960 |
| ccgcgattaa | attccaacat | ggatgctgat ttatatgggt ataaatgggc tcgcgataat | 1020 |
| gtcgggcaat | caggtgcgac | aatctatcga ttgtatggga agcccgatgc gccagagttg | 1080 |
| tttctgaaac | atggcaaagg | tagcgttgcc aatgatgtta cagatgagat ggtcagacta | 1140 |
| aactggctga | cggaatttat | gcctcttccg accatcaagc attttatccg tactcctgat | 1200 |
| gatgcatggt | tactcaccac | tgcgatccct gggaaaacag cattccaggt attagaagaa | 1260 |
| tatcctgatt | caggtgaaaa | tattgttgat gcgctggcag tgttcctgcg ccggttgcat | 1320 |
| tcgattcctg | tttgtaattg | tcctttaac agcgatcgcg tatttcgtct cgctcaggcg | 1380 |
| caatcacgaa | tgaataacgg | tttggttgat gcgagtgatt ttgatgacga gcgtaatggc | 1440 |
| tggcctgttg | aacaagtctg | gaaagaaatg cataagtttt tgccattctc accggattca | 1500 |
| gtcgtcactc | atggtgattt | ctcacttgat aaccttattt ttgacgaggg gaaattaata | 1560 |
| ggttgtattg | atgttggacg | agtcggaatc gcagaccgat accaggatct tgccatccta | 1620 |
| tggaactgcc | tcggtgagtt | ttctccttca ttacagaaac ggctttttca aaaatatggt | 1680 |
| attgataatc | ctgatatgaa | taaattgcag tttcatttga tgctcgatga gttttctaa | 1740 |
| tcagaattgg | ttaattggtt | gtaacactgg cagagcatta cgctgacttg acgggacggc | 1800 |
| ggctttgttg | aataaatcga | acttttgctg agttgaagga tcagatcacg catcttcccg | 1860 |
| acaacgcaga | ccgttccgtg | gcaaagcaaa agttcaaaat caccaactgg tccacctaca | 1920 |
| acaaagctct | catcaaccgt | ggctccctca ctttctggct ggatgatggg gcgattcagg | 1980 |
| cctggtatga | gtcagcaaca | ccttcttcac gaggcagacc tcagcgcctg caggtcgacg | 2040 |
| gatctggggg | atctagcaga | tccgcgaggg gatcgagccc gacatatgcc ccggtttcgt | 2100 |
| tgcgactaac | atgagttctt | ggacaaattt gattggacct gatgagatga tccaacccga | 2160 |
| ggatatagca | aagctcgttc | gtgcagcaat ggaacggcca aaccgtgctt ttgtccccaa | 2220 |
| gaatgaggtg | ctatgcatga | aggaatctac ccgttgatgt ccaacagtct cagggttaat | 2280 |
| gtctatgtat | cttaaataat | gttgtcggta ttttgtaatc tcatatagat tttcactgtg | 2340 |
| cgacgcaaaa | atattaaata | aatattatta ttatctacgt tttgattgag atatcatcaa | 2400 |
| tattataata | aaaatatcca | ttaaacacga tttgatacaa atgacagtca ataatctgat | 2460 |
| ttgaatattt | attaattgta | acgaattaca taaagatcga atagaaaata ctgcactgca | 2520 |
| aatgaaaatt | aacacatact | aataaatgcg tcaaatatct ttgccaagat caagcggagt | 2580 |
| gagggcctca | tatccggtct | cagttacaag cacggtatcc ccgaagcgcg ctccaccaat | 2640 |
| gccctcgaca | tagatgccgg | gctcgacgct gaggacattg cctaccttga gcatggtctc | 2700 |
| agcgccggct | ttaagctcaa | tcccatccca atctgaatat cctatcccgc gcccagtccg | 2760 |
| gtgtaagaac | gggtctgtcc | atccacctct gttgggtgg gcgaagaact ccagcatgag | 2820 |
| atccccgcgc | tggaggatca | tccagccggc gtcccggaaa acgattccga agcccaacct | 2880 |
| ttcatagaag | gcggcggtgg | aatcgaaatc tcgtgatggc aggttgggcg tcgcttggtc | 2940 |
| ggtcatttcg | aacccagag | tccgctcag aagaactcgt caagaaggcg atagaaggcg | 3000 |
| atgcgctgcg | aatcgggagc | ggcgataccg taaagcacga ggaagcggtc agcccattcg | 3060 |
| ccgccaagct | cttcagcaat | atcacgggta gccaacgcta tgtcctgata gcggtccgcc | 3120 |
| acacccagcc | ggccacagtc | gatgaatcca gaaaagcggc catttccac catgatattc | 3180 |
| ggcaagcagg | catcgccatg | ggtcacgacg agatcctcgc cgtcgggcat gcgcgccttg | 3240 |

-continued

```
agcctggcga acagttcggc tggcgcgagc ccctgatgct cttcgtccag atcatcctga    3300
tcgacaagac cggcttccat ccgagtacgt gctcgctcga tgcgatgttt cgcttggtgg    3360
tcgaatgggc aggtagccgg atcaagcgta tgcagccgcc gcattgcatc agccatgatg    3420
gatactttct cggcaggagc aaggtgagat gacaggagat cctgccccgg cacttcgccc    3480
aatagcagcc agtcccttcc cgcttcagtg acaacgtcga gcacagctgc gcaaggaacg    3540
cccgtcgtgg ccagccacga tagccgcgct gcctcgtcct gcagttcatt cagggcaccg    3600
gacaggtcgg tcttgacaaa agaaccgggc gcccctgcg ctgacagccg gaacacggcg    3660
gcatcagagc agccgattgt ctgttgtgcc cagtcatagc cgaatagcct ctccacccaa    3720
gcggccggag aacctgcgtg caatccatct tgttcaatca tgctaaagga tctcgatccc    3780
cgggctgatt ttctcagtct ccagagatgt gtttaaatag gcagtagcct tttgatatca    3840
gccacaagtg tgtgggaatc ttatcttcgg atttcaatta ggaattaacc ttattgaatt    3900
ctcttgaaag gaagtccgca aagtggttgt cggttccttt aatgtgttca acatcaaatg    3960
aatagtggct aagccatgct tgccatctga tgtttcttcc aagtttcgaa tctcctttgt    4020
aattgagatt aacgaaactc ttgaaatgag tattatctgt cctaatcaga aaatgaacag    4080
gagttagata aatactaaat ttctttatag tatttattac cgccaatgtc tctttgtcat    4140
tgctgtggta attcttttct gcagctttaa agctcagatc ttgcaagcga tcgcggcgcg    4200
ccatttaaat gcccgggcgt ttaaacgcgg ccgcttaatt aaggccggcc tgcaggcatg    4260
caagctcgga tctcacctac gatgggggc atcgcaccgg tgagtaatat tgtacggcta    4320
agagcgaatt tggcctgtag acctcaattg cgagcttttct aatttcaaac tattcgggcc    4380
taacttttgg tgtgatgatg ctgactggca ggatatatac cgttgtaatt tgagctcgtg    4440
tgaataagtc gctgtgtatg tttgtttgat tgtttctgtt ggagtgcagc ccatttcacc    4500
ggacaagtcg gctagattga tttagccctg atgaactgcc gaggggaagc catcttgagc    4560
gcggaatggg aatggatttc gttgtacaac gagacgacag aacacccacg ggaccgagct    4620
tcgcaagctt gttgtaactg aaaaggaaa attattgtgc caggcagttg aaagtcagca    4680
ccttttaacg agtgctgaaa tgacggctaa atgggaaacg tatttaaaaa aaatcggtaa    4740
aagagaaggc aatcaagaga actttattac gaatatcaaa aaattcattg ttcatttact    4800
ggaagctgta cctaacgata tagaaaaact aaatttttct gattaccagg aacagaaaga    4860
aaaagaagca gaaaaaagta ttgtaggaaa atgtcctaag tgtggcaaca atattgtatt    4920
aaaaaaatcg ttttatggtt gttcaaatta tcctgaatgt aagtttactt tagctgaaca    4980
ttttagaaag aaaaaactca ccaaaacaaa tgtaaaagaa ttactagagg aaaagaaac    5040 cctggtaaaa ggaatcaaaa cgaaagatag aaagtcctac aatgccgttg taaaaatcgg    5100
agaaaaggga tatattgatt ttatatcttt ctcaaaataa acataaaagc cctttaaaga    5160
gggcttttat atattaatca caaatcactt atcacaaatc acaagtgatt tgtgattgtt    5220
gatgataaaa taagaataag aagaaataga agaagtgag tgattgtggg aaatttaggc    5280
gcacaaaaag aaaacgaaa tgatacacca atcagtgcaa aaaagatat aatgggagat    5340 aagacggttc gtgttcgtgc tgacttgcac catatcataa aaatcgaaac agcaaagaat    5400
ggcggaaacg taaagaagt tatggaaata agacttagaa gcaaacttaa gagtgtgttg    5460
atagtgcagt atcttaaaat tttgtataat aggaattgaa gttaaattag atgctaaaaa    5520
tttgtaatta agaaggagtg attacatgaa caaaaatata aatattctc aaaactttt    5580
```

```
aacgagtgaa aaagtactca accaaataat aaaacaattg aatttaaaag aaaccgatac    5640
cgtttacgaa attggaacag gtaaagggca tttaacgacg aaactggcta aataagtaa    5700 acaggtaacg tctattgaat tagacagtca tctattcaac ttatcgtcag aaaaattaaa    5760
actgaatact cgtgtcactt taattcacca agatattcta cagtttcaat tccctaacaa    5820
acagaggtat aaaattgttg ggagtattcc ttaccattta agcacacaaa ttattaaaaa    5880
agtggttttt gaaagccatg cgtctgacat ctatctgatt gttgaagaag gattctacaa    5940
gcgtaccttg gatattcacc gaacactagg gttgctcttg cacactcaag tctcgattca    6000
gcaattgctt aagctgccag cggaatgctt tcatcctaaa ccaaaagtaa acagtgtctt    6060
aataaaactt acccgccata ccacagatgt tccagataaa tattggaagc tatatacgta    6120
ctttgtttca aaatgggtca atcgagaata tcgtcaactg tttactaaaa atcagtttca    6180
tcaagcaatg aaacacgcca aagtaaacaa tttaagtacc gttacttatg agcaagtatt    6240
gtctattttt aatagttatc tattatttaa cgggaggaaa taattctatg agtcgctttt    6300
gtaaatttgg aaagttacac gttactaaag ggaatgtaga taaattatta ggtatactac    6360
tgacagcttc caaggagcta aagaggtccc tagcgcctac ggggaatttg tatcgataag    6420
gggtacaaat tcccactaag cgctcggggg ctgagaaagc ccagtaagga aacaactgta    6480
ggttcgagtc gcgagatccc ccggaaccaa aggaagtagg ttaaacccgc tccgatcagg    6540
ccgagccacg ccaggccgag aacattggtt cctgtaggca tcgggattgg cggatcaaac    6600
actaaagcta ctggaacgag cagaagtcct ccggccgcca gttgccaggc ggtaaaggtg    6660
agcagaggca cgggaggttg ccacttgcgg gtcagcacgg ttccgaacgc catggaaacc    6720
gcccccgcca ggcccgctgc gacgccgaca ggatctagcg ctgcgtttgg tgtcaacacc    6780
aacagcgcca cgcccgcagt tccgcaaata gcccccagga ccgccatcaa tcgtatcggg    6840
ctacctagca gagcggcaga gatgaacacg accatcagcg gctgcacagc gcctaccgtc    6900
gccgcgaccc cgcccggcag gcggtagacc gaaataaaca acaagctcca gaatagcgaa    6960
atattaagtg cgccgaggat gaagatgcgc atccaccaga ttcccgttgg aatctgtcgg    7020
acgatcatca cgagcaataa acccgccggc aacgcccgca gcagcatacc ggcgaccct    7080 cggcctcgct gttcgggctc cacgaaaacg ccggacagat gcgccttgtg agcgtccttg    7140
gggccgtcct cctgtttgaa gaccgacagc ccaatgatct cgccgtcgat gtaggcgccg    7200
aatgccacga catctcgcaa ccgttcagcg aacgcctcca tgggctttt ctcctcgtgc    7260 tcgtaaacgg acccgaacat ctctggagct ttcttcaggg ccgacaatcg gatctcgcgg    7320
aaatcctgca cgtcggccgc tccaagccgt cgaatctgag ccttaatcac aattgtcaat    7380
tttaatcctc tgtttatcgg cagttcgtag agcgcgccgt gcgcccgagc gatactgagc    7440
gaagcaagtg cgtcgagcag tgcccgcttg ttcctgaaat gccagtaaag cgctggctgc    7500
tgaaccccca gccggaactg accccacaag gccctagcgt ttgcaatgca ccaggtcatc    7560
attgacccag gcgtgttcca ccaggccgct gcctcgcaac tcttcgcagg cttcgccgac    7620
ctgctcgcgc cacttcttca cgcgggtgga atccgatccg cacatgaggc ggaaggtttc    7680
cagcttgagc gggtacggct cccggtgcga gctgaaatag tcgaacatcc gtcgggccgt    7740
cggcgacagc ttgcggtact tctcccatat gaatttcgtg tagtggtcgc cagcaaacag    7800
cacgacgatt tcctcgtcga tcaggacctg gcaacgggac gttttcttgc cacggtccag    7860
gacgcggaag cggtgcagca gcgacaccga ttccaggtgc ccaacgcggt cggacgtgaa    7920
gcccatcgcc gtcgcctgta ggcgcgacag gcattcctcg gccttcgtgt aataccggcc    7980
```

-continued

```
attgatcgac cagcccaggt cctggcaaag ctcgtagaac gtgaaggtga tcggctcgcc    8040
gataggggtg cgcttcgcgt actccaacac ctgctgccac accagttcgt catcgtcggc    8100
ccgcagctcg acgccggtgt aggtgatctt cacgtccttg ttgacgtgga aaatgacctt    8160
gttttgcagc gcctcgcgcg ggattttctt gttgcgcgtg gtgaacaggg cagagcgggc    8220
cgtgtcgttt ggcatcgctc gcatcgtgtc cggccacggc gcaatatcga acaaggaaag    8280
ctgcatttcc ttgatctgct gcttcgtgtg tttcagcaac gcggcctgct tggcctcgct    8340
gacctgtttt gccaggtcct cgccggcggt ttttcgcttc ttggtcgtca tagttcctcg    8400
cgtgtcgatg gtcatcgact tcgccaaacc tgccgcctcc tgttcgagac gacgcgaacg    8460
ctccacggcg gccgatggcg cgggcagggc aggggggagcc agttgcacgc tgtcgcgctc    8520
gatcttggcc gtagcttgct ggaccatcga gccgacggac tggaaggttt cgcggggcgc    8580
acgcatgacg gtgcggcttg cgatggtttc ggcatcctcg gcggaaaacc ccgcgtcgat    8640
cagttcttgc ctgtatgcct tccggtcaaa cgtccgattc attcaccctc cttgcgggat    8700
tgccccgact cacgccgggg caatgtgccc ttattcctga tttgacccgc ctggtgcctt    8760
ggtgtccaga taatccacct tatcggcaat gaagtcggtc ccgtagaccg tctggccgtc    8820
cttctcgtac ttggtattcc gaatcttgcc ctgcacgaat accagctccg cgaagtcgct    8880
cttcttgatg gagcgcatgg ggacgtgctt ggcaatcacg cgcacccccc ggccgttttta   8940
gcggctaaaa aagtcatggc tctgccctcg ggcggaccac gcccatcatg accttgccaa    9000
gctcgtcctg cttctcttcg atcttcgcca gcagggcgag gatcgtggca tcaccgaacc    9060
gcgccgtgcg cgggtcgtcg gtgagccaga gtttcagcag gccgcccagg cggcccaggt    9120
cgccattgat gcgggccagc tcgcggacgt gctcatagtc cacgacgccc gtgattttgt    9180
agccctggcc gacggccagc aggtaggccg acaggctcat gccggccgcc gccgcctttt    9240
cctcaatcgc tcttcgttcg tctggaaggc agtacacctt gataggtggg ctgcccttcc    9300
tggttggctt ggtttcatca gccatccgct tgccctcatc tgttacgccg gcggtagccg    9360
gccagcctcg cagagcagga ttcccgttga gcaccgccag gtgcgaataa gggacagtga    9420
agaaggaaca cccgctcgcg ggtgggccta cttcacctat cctgcccggc tgacgccgtt    9480
ggatacacca aggaaagtct acacgaaccc tttggcaaaa tcctgtatat cgtgcgaaaa    9540
aggatggata taccgaaaaa atcgctataa tgaccccgaa gcagggttat gcagcggaaa    9600
agatccgtcg acccttccg acgctcaccg ggctggttgc cctcgccgct gggctggcgg    9660
ccgtctatgg ccctgcaaac cgccagaaa cgccgtcgaa gccgtgtgcg agacaccgcg    9720
gccgccggcg ttgtggatac ctcgcggaaa acttggccct cactgacaga tgaggggcgg    9780
acgttgacac ttgaggggcc gactcacccg gcgcggcgtt gacagatgag gggcaggctc    9840
gatttcggcc ggcgacgtgg agctggccag cctcgcaaat cggcgaaaac gcctgatttt    9900
acgcgagttt cccacagatg atgtggacaa gcctggggat aagtgccctg cggtattgac    9960
acttgagggg cgcgactact gacagatgag gggcgcgatc cttgacactt gaggggcaga   10020
gtgctgacag atgaggggcg cacctattga catttgaggg gctgtccaca ggcagaaaat   10080
ccagcatttg caaggtttc cgcccgtttt tcggccaccg ctaacctgtc ttttaacctg    10140
cttttaaacc aatatttata aaccttgttt ttaaccaggg ctgcgccctg tgcgcgtgac   10200
cgcgcacgcc gaagggggt gccccccctt ctcgaaccct cccggccgc taacgcggc    10260
ctcccatccc cccagggggct gcgcccctcg gccgcgaacg gcctcacccc aaaaatggca   10320
```

```
                                                                   gcc                        10323

<210> SEQ ID NO 12
<211> LENGTH: 1371
<212> TYPE: DNA
<213> ORGANISM: Artificial Sequence
<220> FEATURE:
<223> OTHER INFORMATION: Description of Artificial Sequence:redesigned
      gene for Aspergillus palmitoyl-CoA desaturase
<221> NAME/KEY: CDS
<222> LOCATION: (1)..(1368)

<400> SEQUENCE: 12 atg gct agc gca cca acg gcg gac atc agg gct agg gcg cca gag gcg        48
Met Ala Ser Ala Pro Thr Ala Asp Ile Arg Ala Arg Ala Pro Glu Ala
 1               5                  10                  15 aag aag gtt cac atc gct gac acg gcg atc aac agg cat aac tgg tac        96
Lys Lys Val His Ile Ala Asp Thr Ala Ile Asn Arg His Asn Trp Tyr
            20                  25                  30 aaa cat gtg aat tgg ctc aat gtg ttc ctg atc atc ggg atc cct ttg       144
Lys His Val Asn Trp Leu Asn Val Phe Leu Ile Ile Gly Ile Pro Leu
        35                  40                  45 tat ggg tgc att caa gcg ttc tgg gtg cca ctc caa ctg aag act gcg       192
Tyr Gly Cys Ile Gln Ala Phe Trp Val Pro Leu Gln Leu Lys Thr Ala
50                  55                  60 atc tgg gca gtg atc tac tac ttc ttc acc ggt cta ggg atc acg gct       240
Ile Trp Ala Val Ile Tyr Tyr Phe Phe Thr Gly Leu Gly Ile Thr Ala
 65                  70                  75                  80 ggg tat cat agg ctc tgg gct cac tgc tcg tac tcg gca acc cta cct       288
Gly Tyr His Arg Leu Trp Ala His Cys Ser Tyr Ser Ala Thr Leu Pro
                85                  90                  95 ttg agg att tgg cta gct gca gtt ggt gga ggt gca gtc gaa ggc tca       336
Leu Arg Ile Trp Leu Ala Ala Val Gly Gly Gly Ala Val Glu Gly Ser
            100                 105                 110 ata cgc tgg tgg gct cgg gat cac agg gct cac cac cgc tac acc gac       384
Ile Arg Trp Trp Ala Arg Asp His Arg Ala His His Arg Tyr Thr Asp
        115                 120                 125 acc gac aaa gat ccg tac tcc gtt cgg aag ggt ctg ctc tac tct cac       432
Thr Asp Lys Asp Pro Tyr Ser Val Arg Lys Gly Leu Leu Tyr Ser His
    130                 135                 140 ctt ggc tgg atg gtg atg aag cag aac ccg aag cgc att ggc cgc act       480
Leu Gly Trp Met Val Met Lys Gln Asn Pro Lys Arg Ile Gly Arg Thr
145                 150                 155                 160 gac att tcc gac ctc aat gag gat ccc gtg gtt gtc tgg caa cac cgc       528
Asp Ile Ser Asp Leu Asn Glu Asp Pro Val Val Val Trp Gln His Arg
                165                 170                 175 aac tac ctg aag gtg gtg ttc acg atg gga ttg gct gtg ccg atg ctt       576
Asn Tyr Leu Lys Val Val Phe Thr Met Gly Leu Ala Val Pro Met Leu
            180                 185                 190 gtt gct gga ctt gga tgg ggt gac tgg ttg ggc ggc ttt gtg tat gcg       624
Val Ala Gly Leu Gly Trp Gly Asp Trp Leu Gly Gly Phe Val Tyr Ala
        195                 200                 205 ggc atc ctg cgc atc ttc ttc gtc caa cag gcg act ttc tgt gtc aac       672
Gly Ile Leu Arg Ile Phe Phe Val Gln Gln Ala Thr Phe Cys Val Asn
    210                 215                 220 tca ttg gcc cac tgg ctg ggt gac cag ccc ttt gat gac cgc aac tca       720
Ser Leu Ala His Trp Leu Gly Asp Gln Pro Phe Asp Asp Arg Asn Ser
225                 230                 235                 240 cct agg gac cat gtg atc acc gct ctg gtc acc ctt gga gag ggc tac       768
Pro Arg Asp His Val Ile Thr Ala Leu Val Thr Leu Gly Glu Gly Tyr
                245                 250                 255
```

-continued

```
cac aac ttt cac cat gag ttc ccc tcg gac tac cgc aat gcc att gaa      816
His Asn Phe His His Glu Phe Pro Ser Asp Tyr Arg Asn Ala Ile Glu
            260                 265                 270 tgg cac cag tat gat ccg acc aag tgg tcc atc tgg gcc tgg aag caa      864
Trp His Gln Tyr Asp Pro Thr Lys Trp Ser Ile Trp Ala Trp Lys Gln
        275                 280                 285 ctt ggg ctt gcc tac gac ctc aag aag ttt agg gcc aac gag ata gag      912
Leu Gly Leu Ala Tyr Asp Leu Lys Lys Phe Arg Ala Asn Glu Ile Glu
    290                 295                 300 aag ggg agg gtc caa cag ctc cag aag aag ctt gac cgc aaa cgg gcc      960
Lys Gly Arg Val Gln Gln Leu Gln Lys Lys Leu Asp Arg Lys Arg Ala
305                 310                 315                 320 act ctg gat tgg ggc acc cct ctt gac caa ctc cct gtc atg gag tgg     1008
Thr Leu Asp Trp Gly Thr Pro Leu Asp Gln Leu Pro Val Met Glu Trp
                325                 330                 335 gat gac tac gtg gag caa gcc aag aac ggg agg ggt ctg gtg gcc att     1056
Asp Asp Tyr Val Glu Gln Ala Lys Asn Gly Arg Gly Leu Val Ala Ile
            340                 345                 350 gcc ggt gtt gtc cat gat gtc aca gac ttc atc aaa gac cac ccg ggt     1104
Ala Gly Val Val His Asp Val Thr Asp Phe Ile Lys Asp His Pro Gly
        355                 360                 365 ggc aag gcc atg ata agc tcc ggc att ggg aag gat gcc acc gcc atg     1152
Gly Lys Ala Met Ile Ser Ser Gly Ile Gly Lys Asp Ala Thr Ala Met
    370                 375                 380 ttc aac ggc ggc gtg tac tac cac agc aac gcc gcc cac aac ctc ctg     1200
Phe Asn Gly Gly Val Tyr Tyr His Ser Asn Ala Ala His Asn Leu Leu
385                 390                 395                 400 agc aca atg cgt gtt ggt gtg atc cgc ggc ggc tgt gag gtc gaa atc     1248
Ser Thr Met Arg Val Gly Val Ile Arg Gly Gly Cys Glu Val Glu Ile
                405                 410                 415 tgg aaa cgg gcc cag aag gag aac gtg gag tac gtg cgt gat ggc tct     1296
Trp Lys Arg Ala Gln Lys Glu Asn Val Glu Tyr Val Arg Asp Gly Ser
            420                 425                 430 ggc cag agg gtc att cgt gcc ggc gag cag cca acg aag ata cca gaa     1344
Gly Gln Arg Val Ile Arg Ala Gly Glu Gln Pro Thr Lys Ile Pro Glu
        435                 440                 445 ccg att ccc aca gca gat gcg gcg tga                                  1371
Pro Ile Pro Thr Ala Asp Ala Ala
    450                 455
```

MODIFICATION OF FATTY ACID COMPOSITION IN PLANTS BY EXPRESSION OF A FUNGAL ACYL-COA DESATURASE

CROSS-REFERENCE TO RELATED APPLICATION

This patent application claims priority from a U.S. Provisional Patent Application Serial No. 60/079,840, filed Mar. 30, 1998.

FIELD OF INVENTION

This invention relates to the preparation and use of nucleic acid fragments or genes which encode fungal palmitoyl-CoA Δ-9 desaturase enzymes to create transgenic plants having altered oil profiles.

BACKGROUND OF THE INVENTION

Plant-produced oils can be found in a wide variety of products including lubricants and foods. Interestingly, different plant species synthesize various oil types. For example, coconut and palm plants produce oils that are abundant in fatty acids having medium chain lengths (10–12 carbon atoms). These oils are used in manufacturing soaps, detergents and surfactants, and represent a U.S. market size greater than $350 million per year. Other plants, such as rape, produce oils abundant in long chain fatty acids (22 carbon atoms) and are used as lubricants and anti-slip agents. Additional applications of plant oils include their use in plasticizers, coatings, paints, varnishes and cosmetics (Volker et al., (1992) Science 257:72–74; Ohlrogge, (1994) Plant Physiol. 104:821–826). However, the predominant use of plant oils is in the production of food and food products.

Over the years, vegetable-derived oils have gradually replaced animal-derived oils and fats as the major source of dietary fat intake. However, saturated fat intake in most industrialized nations has remained at about 15% to 20% of total caloric consumption. In efforts to promote healthier lifestyles, the United States Department of Agriculture (USDA) has recently recommended that saturated fats make up less than 10% of daily caloric intake. To facilitate consumer awareness, current labeling guidelines issued by the USDA now require total saturated fatty acid levels be less than 1.0 g per 14 g serving to receive the "low-sat" label and less than 0.5 g per 14 g serving to receive the "no-sat" label. This means that the saturated fatty acid content of plant oils needs to be less than 7% and 1.75% to receive the "low sat" and "no sat" label, respectively. Since issuance of these guidelines, there has been a surge in consumer demand for "low-sat" oils. To date, this has been met principally with canola oil, and to a much lesser degree with sunflower and safflower oils.

The characteristics of oils, whether of plant or animal origin, are determined predominantly by the number of carbon and hydrogen atoms, as well as the number and position of double bonds comprising the fatty acid chain. Most oils derived from plants are composed of varying amounts of palmitic (16:0), stearic (18:0), oleic (18:1), linoleic (18:2) and linolenic (18:3) fatty acids. Conventionally, palmitic and stearic acids are designated as "saturated" since the fatty acid chains have 16 and 18 carbon atoms, respectively, and no double bonds. They therefore contain the maximal number of hydrogen atoms possible. However, oleic, linoleic, and linolenic are 18-carbon fatty acid chains having one, two, and three double bonds, respectively, therein. Oleic acid is typically considered a mono-unsaturated fatty acid, whereas linoleic and linolenic are considered to be poly-unsaturated fatty acids.

Saturated fatty acids are linear molecules and tend to form self-stacked structures thereby resulting in high melting temperatures; a characteristic that is quite desirable when producing foods like chocolate. Animal fats, which are also solid at room temperature, are another readily available source of saturated fatty acids. However, use of said oil is often discouraged due to the high levels of cholesterol associated therewith. In comparison, unsaturated fatty acid chains are nonlinear due to bending induced by double bond insertion. The bending of the molecule impedes the ability of the fatty acid chains to stack thus causing them to remain fluid at lower temperatures. Vegetable oils, for example, are high in unsaturated fatty acids, and therefore are typically liquid at room temperature. Furthermore, saturated fatty acid can be modified to become unsaturated fatty acids by removal of hydrogen atoms and insertion of double bonds between two carbon atoms on the fatty acid chain. Desaturation can be achieved either enzymatically or chemically and decreases melting points due to the inability of the fatty acid molecules to self-stack.

The total saturated fatty acid level of corn oil, averaging about 13.9%, does not meet the current labeling guidelines discussed above. On average, corn oil is comprised of 11.5% palmitic acid, 2.2% stearic acid, 26.6% oleic acid, 58.7% linoleic acid, and 0.8% linolenic acid. Corn oil also contains 0.2% arachidic acid, a twenty-carbon saturated fatty acid (Dunlap et. al., (1995) J. Amer. Oil Chem. Soc. 72:981–987). The composition of corn oil instills it with properties that are most desirable in edible oils. These include properties such as heat stability, flavor, and long shelf life. However, consumer demand for "low sat" oils has resulted in a significant decrease in corn oil utilization and thus decreased market share. Therefore, a corn oil with modified levels of saturated fatty acids is highly desirable and would have practical use in that it would meet the consumer demand for healthier oils while having most or all of the properties that made corn oil a popular and preferred oil in the past.

Corn is typically not considered to be an oil crop as compared to soybean, canola, sunflower and the like. In fact, the oil produced and extracted from corn is considered to be a byproduct of the wet milling process used in starch extraction. Because of this, there has been little interest in modifying the saturate levels of corn oil until those efforts disclosed herein.

As disclosed herein, saturate levels of fatty acids comprising plant oils can be altered by expressing a fungal palmitate-CoA Δ-9 desaturase within a plant cell. These proteins most likely enzymatically desaturate palmitate-CoA molecules by removing two hydrogen atoms and adding a double bond between the $9^{th}$ and $10^{th}$ carbon atoms from the CoA portion of the molecule, thus producing palmitoleic-CoA ($16:1^{\Delta 9}$). The palmitoleic-CoA is ultimately incorporated into seed oil thus lowering the total saturate levels of said oil.

SUMMARY OF THE INVENTION

In the present invention, a gene encoding a fungal palmitate-CoA Δ-9 desaturase has been isolated and cloned from *Aspergillus nidulans*. The saturate level of oils found in plant cells can be altered by expressing said palmitate-CoA Δ-9 desaturase from *Aspergillus nidulans*.

One aspect of the disclosed invention is a gene encoding said palmitate-CoA Δ-9 desaturase, said gene being isolated and purified from *Aspergillus nidulans*.

An additional aspect of the present invention relates to producing a gene wherein the codon bias of a gene from a non-plant source has been modified to look similar to genes from a plant source.

Another aspect of the invention relates to altering oil saturate levels within a plant cell by expressing said genes encoding palmitate-CoA Δ-9 desaturase from *Aspergillus nidulans*. Genes disclosed herein can be used to alter saturate levels by placing said genes in the sense orientation. Plants cells being transformed with genes encoding palmitate-CoA Δ-9 desaturase from *Aspergillus nidulans* in the sense orientation results in the oils of said plants having increased 16:1 levels and decreased total saturate levels over non-transformed plants.

An additional aspect of the present invention is the production of chimeric genes using the genes disclosed herein encoding for palmitoyl CoA-Δ-9 desaturase in combination with promoter regulatory elements and the use of said chimeric genes within a plant cell.

Yet an additional aspect of the present invention is the transformation of plant species disclosed herein with said chimeric genes.

Other aspects, embodiments, advantages, and features of the present invention will become apparent from the following specification.

DETAILED DESCRIPTION OF THE INVENTION

The present invention relates to methods and compositions for obtaining transgenic plants wherein plant oils produced thereby have altered saturate levels. The following phrases and terms are defined below:

By "altered saturate levels" is meant that the level of total saturated fatty acids of a plant oil produced by a modified plant is different from that of a normal or non-modified plant.

By "cDNA" is meant DNA that is complementary to and derived from a mRNA.

By "chimeric DNA construction" is meant a recombinant DNA containing genes or portions thereof from one or more species.

By "complementarity" is meant a nucleic acid that can form hydrogen bond(s) with other nucleic acid sequences either through traditional Watson-Crick or other non-traditional types of base paired interactions.

By "constitutive promoter" is meant promoter elements that direct continuous gene expression in all cell types and at all times (i.e., actin, ubiquitin, CaMV 35S, 35T, and the like).

By "developmental specific" promoter is meant promoter elements responsible for gene expression at specific plant developmental stages, such as in early or late embryogenesis and the like.

By "enhancer" is meant nucleotide sequence elements which can stimulate promoter activity such as those from maize streak virus (MSV) protein leader sequence, alfalfa mosaic virus protein leader sequence, alcohol dehydrogenase intron 1, and the like.

By "expression" as used herein, is meant the transcription and stable accumulation of mRNA inside a plant cell. Expression of genes also involves transcription of the gene to create mRNA and translation of the mRNA into precursor or mature proteins.

By "foreign" or "heterologous gene" is meant a gene encoding a-protein whose exact amino acid sequence is not normally found in the host cell, but is introduced by standard gene transfer techniques.

By "gene" is meant to include all genetic material involved in protein expression including chimeric DNA constructions, genes, plant genes and portions thereof, and the like.

By "genome" is meant genetic material contained in each cell of an organism and/or virus and the like.

By "inducible promoter" is meant promoter elements which are responsible for expression of genes in response to a specific signal such as: physical stimuli (heat shock genes); light (RUBP carboxylase); hormone (Em); metabolites, chemicals, stress and the like.

By "modified plant" is meant a plant wherein the gene, mRNA, or protein from *Aspergillus nidulans* palmitate-CoA Δ-9 desaturase is present.

By "plant" is meant a photosynthetic organism including both eukaryotes and prokaryotes.

By "promoter regulatory element" is meant nucleotide sequence elements within a nucleic fragment or gene which controls the expression of that nucleic acid fragment or gene. Promoter sequences provide the recognition for RNA polymerase and other transcriptional factors required for efficient transcription. Promoter regulatory elements from a variety of sources can be used efficiently in plant cells to express gene constructs. Promoter regulatory elements are also meant to include constitutive, tissue-specific, developmental-specific, inducible promoters and the like. Promoter regulatory elements may also include certain enhancer sequence elements and the like that improve transcriptional efficiency.

By "tissue-specific" promoter is meant promoter elements responsible for gene expression in specific cell or tissue types, such as the leaves or seeds (i.e., zein, oleosin, napin, ACP, globulin and the like).

By "transgenic plant" is meant a plant expressing a chimeric gene introduced through transformation efforts.

In plant cells, fatty acids are made as acyl-acyl carrier protein (acyl-ACP) substrates and are elongated by various enzymes through the addition of malonyl-ACP to make acyl-ACP molecules ranging in length from 2 to 18 carbon atoms. Afterwards, acyl-ACP thioesterases catalyze the hydrolytic cleavage of palmitic acid, stearic acid, and oleic acid from ACP, in a somewhat selective although not specific manner, thus producing a free fatty acids. The fatty acid molecules move out of the plastid into the cytoplasm where they are eventually modified into acyl-CoA molecules. Said molecules are then incorporated onto the triglyceride oil fraction. It has been discovered by applicants as disclosed herein that desaturation of an acyl-CoA molecule, wherein said molecule is preferably stearoyl-CoA and most preferably palmitate-CoA, can reduce saturate levels in the triglyceride oil fraction. Said desaturation most preferably results in the production and accumulation of palmitoleic acid ($16:1^{\Delta-9}$). Said desaturation may also result in a decrease in palmitic and stearic acid in the triglyceride oil fraction.

In corn seed oil, the predominant fatty acids are linoleic acid (18:2 at about 59%), oleic acid (18:1 at about 26%) and palmitic (16:0 at about 11%), with stearic acid (18:0) generally comprising about 2.5% or less (Glover and Mertz, (1987) in: Nutritional Quality of Cereal Grains: genetic and agronomic improvement., p.183–336, (eds. Olson, R. A. and Frey, K. J.) Amer. Soc. Agronomy, Inc., Madison, Wis.; Fitch-Haumann, (1985) J. Am. Oil. Chem. Soc.

62:1524–1531). Biosynthesis of fatty acids in plant cells is initiated in the plastids where they are synthesized as acyl-ACP thioesters by a fatty acid synthase complex. More specifically, fatty acid production is accomplished by a series of condensation reactions involving addition of malonyl-ACP sequentially to a growing fatty acid-ACP chain by the enzyme β-ketoacyl-ACP synthase I (KAS I). Most fatty acid-ACP units reach carbon chain lengths of 16 and are then elongated to 18 carbon units by KAS II. The vast majority of C18 fatty acids become desaturated by stearoyl-ACP Δ-9 desaturase at the C9 position from the carboxyl end to produce oleyl-ACP.

Both saturated and unsaturated fatty acid-ACP units are hydrolyzed by acyl-ACP thioesterases to produce free fatty acids. These free fatty acids then cross the plastid membrane to the cytosol of the cell where they are modified by addition of a CoA moiety. Afterwards, said fatty acids are incorporated into plant oils (Somerville and Browse, (1991) Science 252:80–87; Browse and Sommerville (1991) Annu. Rev. Plant Physiol. Plant Mol. Biol. 42:467–506; Harwood (1989) Critical Reviews in Plant Sci. 8:1–43; Chasan (1995) Plant Cell 7:235–237; Ohlrogge (1994) Plant Physiol. 104:821–826).

The palmitate-CoA Δ-9 desaturase from Aspergillus nidulans desaturates palmitic acid at the C9 position relative to the carboxyl end most likely after the point of modification with Co-A. In plant cells, this most likely occurs before being incorporated into the triglyceride fraction of the oil. Therefore, expressing palmitate-CoA Δ-9 desaturase from Aspergillus nidulans in plant-cells will cause a decrease in the saturate levels of the oil produced by said plant.

The palmitate-CoA Δ-9 desaturase from Aspergillus nidulans disclosed herein can be used to modify saturate levels in oil in both monocotyledonous and dicotyledonous plants. In dicotyledonous plants, expression of said desaturase preferably results in a decrease in 16:0 and 18:0 levels found in oil derived from said plants. More preferably, expression of said desaturase results in increased levels of 16:1 fatty acid in said oil. In monocotyledonous plants, expression of said desaturase preferably results in decreased levels of 18:0 and more preferably, increased levels of 16:1 found in the said oil. It is not applicants intention, however, to limit said gene expression exclusively to plants in that said desaturase and genes thereof can be expressed and used to modify lipid contents in both yeast and bacteria.

As further described herein, an Aspergillus palmitate-CoA Δ-9 desaturase can be used to modify the saturate levels in oils produced by transgenic plants. Preferably, genes and nucleic fragments encoding the palmitate-CoA Δ-9 desaturase are derived from Aspergillus nidulans. More preferably, genes encoding palmitate-CoA Δ-9 desaturase from Aspergillus nidulans are those disclosed herein as SEQ ID NO:5 and SEQ ID NO:12, said genes encoding a protein having an amino acid sequence as disclosed herein as SEQ ID NO:6.

One method by which plant oils can be modified is by expressing the palmitate-CoA Δ-9 desaturase from Aspergillus nidulans in a dicotyledonous plant. This can be achieved by placing the genes or nucleic acid fragments encoding said proteins in the sense orientation 3' to a promoter regulatory element of choice followed by a transcriptional terminator at the 3' end of said gene thus producing a chimeric gene construct. These chimeric genes can then be transformed into plants, thereby producing plant oils having altered saturate levels relative to nontransformed controls. Expressing the palmitate-CoA Δ-9 desaturase as disclosed herein from Aspergillus nidulans in dicotyledonous plants results in plant oils derived therefrom having 16:1 levels as a percentage of the total fatty acid from about 0.23 to about 4.65%; preferably from about 3.01 to about 4.65%; more preferably from about 4.07 to about 4.65%, with about 4.65% being most preferred. The total saturate levels range preferably from about 9.8 to about 12.5% with about 9.8% being most preferred.

Another method by which plant oils can be modified is by expressing the palmitate-CoA Δ-9 desaturase from Aspergillus nidulans in a monocotyledonous plant. As with dicotyledonous plants, this can be achieved by placing the genes or nucleic acid fragments encoding said proteins in the sense orientation 3' to a promoter regulatory element of choice followed by a transcriptional terminator at the 3'end of said gene thus producing a chimeric gene construct. These chimeric genes can then be transformed into plants, thereby producing plant oils having altered saturate levels relative to nontransformed controls. Expressing the palmitate-CoA Δ-9 desaturase from Aspergillus nidulans in monocotyledonous plants results in plant oils derived therefrom to have 16:1 levels from about 0.4 to about 3.2%; preferably from about 1.2 to about 3.2%, with about 3.2% being most preferred.

As further disclosed herein, chimeric gene constructs encoding palmitate-CoA Δ-9 desaturase from Aspergillus nidulans can be transformed in other oilseed crops to modify the saturate levels therein. Said oilseed crop plant species which may be modified include but are not limited to soybean, Brassicaceae sp., canola, rape, sunflower, flax, safflower, coconut, palm, olive, peanut, cotton, castor bean, coriander, Crambe sp., Cuphea sp., Euphorbia sp., Oenothera sp., jojoba, Lesquerella sp., marigold, Limnanthes sp., Vernonia sp., Sinapis alba, and cocoa, with maize being most preferred. Most if not all of these plant species have been previously transformed by those having ordinary skill in the art.

To obtain high expression of heterologous genes in plants it may be preferred to reengineer said genes so that they are more efficiently expressed in the cytoplasm of plant cells. Maize is one such plant where it may be preferred to reengineer the heterologous gene(s) prior to transformation to increase the expression level thereof in said plant. Therefore, an additional step in the design of genes encoding said palmitate-CoA Δ-9 desaturase from Aspergillus nidulans is the designed reengineering of a heterologous gene for optimal expression.

One reason for the reengineering the Δ-9 Co-A desaturase gene from Aspergillus nidulans for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding palmitate-CoA Δ-9 desaturase from Aspergillus nidulans for maize expression, more preferably referred to as plant optimized gene(s), is to generate a DNA sequence having a higher G+C content, and preferably one close to that of maize genes coding for metabolic enzymes.

Another goal in the design of the plant optimized gene(s) encoding palmitate-CoA Δ-9 desaturase from *Aspergillus nidulans* is to generate a DNA sequence in which the sequence modifications do not hinder translation.

The table below (Table 1) illustrates how high the G+C content is in maize. For the data in Table 1, coding regions of the genes were extracted from GenBank (Release 71) entries, and base compositions were calculated using the MacVector™ program (IBI, New Haven, Conn.). Intron sequences were ignored in the calculations.

Due to the plasticity afforded by the redundancy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

TABLE 1

Compilation of G + C contents of protein coding regions of maize genes.

| Protein Class[a] | Range % G + C | Mean % G + C[b] |
|---|---|---|
| Metabolic Enzymes (76) | 44.4–75.3 | 59.0 (±8.0) |
| Structural Proteins (18) | 48.6–70.5 | 63.6 (±6.7) |
| Regulatory Proteins (5) | 57.2–68.9 | 62.0 (±4.9) |
| Uncharacterized Proteins (9) | 41.5–70.3 | 64.3 (±7.2) |
| All Proteins (108) | 44.4–75.3 | 60.8 (±5.2) |

[a]Number of genes in class given in parentheses.
[b]Standard deviations given in parentheses.
[c]combined groups mean ignored in mean calculation.

In reengineering genes encoding palmitate-CoA Δ-9 desaturase from *Aspergillus nidulans* for maize expression, the codon bias of the plant has been determined. The codon bias for maize is the statistical codon distribution that the plant uses for coding its proteins and the preferred codon usage is shown in Table 2. After determining the bias, the percent frequency of the codons in the gene(s) of interest is determined. The primary codons preferred by the plant should be determined as well as the second and third choice of preferred codons. Afterwards, the amino acid sequence of palmitate-CoA Δ-9 desaturase from *Aspergillus nidulans* is reverse translated so that the resulting nucleic acid sequence codes for exactly the same protein as the native gene wanting to be heterologously expressed. The new DNA sequence is designed using codon bias information so that it corresponds to the most preferred codons of the desired plant. The new sequence is then analyzed for restriction enzyme sites that might have been created by the modification. The identified sites are further modified by replacing the codons with second or third choice with preferred codons. Other sites in the sequence which could is affect transcription or translation of the gene of interest are the exon:intron 5' or 3' junctions, poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

It is preferred that the plant optimized gene(s) encoding palmitate-CoA Δ-9 desaturase from *Aspergillus nidulans* contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 2. The method described above enables one skilled in the art to modify gene(s) that are foreign to a particular plant so that the genes are optimally expressed in plants. The method is further illustrated in pending PCT application WO 97/13402, which is incorporated herein by reference.

In order to design plant optimized genes encoding palmitate-CoA Δ-9 desaturase from *Aspergillus nidulans*, the amino acid sequence of said protein is reverse translated into a DNA sequence utilizing a non-redundant genetic code established from a codon bias table compiled for the gene sequences for the particular plant, as shown in Table 2.

The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA. Said sequence produced using the methods described herein is disclosed as SEQ ID NO:12.

In another aspect of the invention, genes encoding the palmitate-CoA Δ-9 desaturase from *Aspergillus nidulans* are expressed from transcriptional units inserted into the plant genome. Preferably, said transcriptional units are recombinant vectors capable of stable integration into the plant genome and selection of transformed plant lines expressing mRNA encoding for said desaturase proteins are expressed either by constitutive or inducible promoters in the plant cell. Once expressed, the mRNA is translated into proteins, thereby incorporating amino acids of interest into protein. The genes encoding palmitate-CoA Δ-9 desaturase from *Aspergillus nidulans* expressed in the plant cells can be under the control of a constitutive promoter, a tissue-specific promoter or an inducible promoter as described herein.

TABLE 2

Preferred amino acid codons for proteins expressed in maize.

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |

TABLE 2-continued

Preferred amino acid codons
for proteins expressed in maize.

| Amino Acid | Codon* |
|---|---|
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

Several techniques exist for introducing foreign recombinant vectors into plant cells, and for obtaining plants that stably maintain and express the introduced gene. Such techniques include acceleration of genetic material coated onto microparticles directly into cells (U.S. Pat. No. 4,945,050 to Cornell and U.S. Pat. No. 5,141,131 to DowElanco, now Dow AgroSciences). In addition, plants may be transformed using Agrobacterium technology, see U.S. Pat. No. 5,177,010 to University of Toledo, U.S. Pat. No. 5,104,310 to Texas A&M, European Patent Application 0131624B1, European Patent Applications 120516, 159418B1 and 176, 112 to Schilperoot, U.S. Pat. Nos. 5,149,645, 5,469,976, 5,464,763 and 4,940,838 and 4,693,976 to Schilperoot, European Patent Applications 116718, 290799, 320500 all to Max is Planck, European Patent Applications 604662, 627752 and U.S. Pat. No. 5,591,616 to Japan Tobacco, European Patent Applications 0267159, and 0292435 and U.S. Pat. No. 5,231,019 all to Ciba Geigy, now Novartis, U.S. Pat. Nos. 5,463,174 and 4,762,785 both to Calgene, and U.S. Pat. Nos. 20 5,004,863 and 5,159,135 both to Agracetus. Other transformation technology includes whiskers technology, see U.S. Pat. Nos. 5,302,523 and 5,464,765 both to Zeneca. Electroporation technology has also been used to transform plants, see WO 87/06614 to Boyce Thompson Institute, U.S. Pat. Nos. 5,472,869 and 5,384,253 both to Dekalb, WO9209696 and WO9321335 both to Plant Genetic Systems. Furthermore, viral vectors can also be used in produce transgenic plants expressing the protein of interest. For example, monocotyledonous plant can be transformed with a viral vector using the methods described in U.S. Pat. No. 5,569,597 to Mycogen and Ciba-Giegy, now Novartis, as well as U.S. Pat. Nos. 5,589,367 and 5,316,931, both to Biosource. All of these transformation patents and publications are incorporated herein by reference.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform Agrobacterium mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation.

Where Agrobacterium is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the Agrobacterium host is not critical to this invention. The Ti or Ri plasmid containing the T-DNA for recombination may be capable or incapable of causing gall formation, and is not critical to said invention so long as the vir genes are present in said host.

In some cases where Agrobacterium is used for transformation, the expression construct being within the T-DNA borders will be inserted into the plasmid pDAB1542 as described herein or into a broad spectrum vector such as pRK2 or derivatives thereof as described in Ditta et al., (PNAS USA (1980) 77:7347–7351 and EPO 0 120 515, which are incorporated herein by reference. Included within the expression construct and the T-DNA will be one or more markers as described herein which allow for selection of transformed Agrobacterium and transformed plant cells. The particular marker employed is not essential to this invention, with the preferred marker depending on the host and construction used.

For transformation of plant cells using Agrobacterium, explants may be combined and incubated with the transformed Agrobacterium for sufficient time to allow transformation thereof. After transformation, the agrobacteria are killed by selection with the appropriate antibiotic and plant cells are cultured with the appropriate selective medium. Once calli are formed, shoot formation can be encourage by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations as well as provide a source for oil isolation. Regardless of transformation technique, the gene encoding palmitoyl-CoA Δ-9 desaturase from *Aspergillus nidulans* is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, and the like. Almost all plant tissues may be transformed during dedifferentiation using appropriate techniques described herein.

Another variable is the choice of a selectable marker. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialophos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Weising et al. Ann. Rev. Genetics, 22, 421 (1988), which is incorporated herein by reference. Preferred reporter genes include the beta-glucuronidase (GUS) of the uida locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uida locus of *E. coli* as described by Jefferson et al., (1987 Biochem. Soc. Trans. 15, 17–19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see PCT/US96/1682; WO 97/13402 published Apr. 17, 1997) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters and tissue specific promoters.

Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan.

Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plants' development as well as active in plant tissues and organs. Examples of such include but are not limited to pollen-specific, embryo specific, corn silk specific, cotton fiber specific, root specific, seed endosperm specific promoter regulatory elements and the like. Under certain circumstances it may be desirable to use an inducible promoter regulatory element, which is responsible for expression of genes in response to a specific signal, such as: physical stimulus (heat shock genes); light (RUBP carboxylase); hormone (Em); metabolites; chemical; and stress. Other desirable transcription and translation elements that function in plants may be used. Numerous plant-specific gene transfer vectors are known in the art.

One of the issues regarding exploiting transgenic plants having altered saturate levels is the expression of multiple chimeric genes at once. European Patent Application 0400246A1 describes transformation of two Bt genes in a plant; however, these could be any two genes or fragments thereof in either the sense or antisense orientation. For example, commercially available hybrids have now been produced having stacked traits such as herbicide and insect resistance. The options could include but are not limited to genes and fragments encoding the palmitoyl-CoA Δ-9 desaturase from *Aspergillus nidulans* with acyl-ACP thioesterase genes or genes encoding proteins such as stearoyl-ACP desaturase, β-ketoacyl synthase II and the like, as well as genes to impart insect control or herbicide resistance. Another way to produce a transgenic plant having multiple traits is to produce two plants, with each plant containing the oil modifying gene of interest. These plants can then be back-crossed using traditional plant breeding techniques available and well-known to those skilled in the art to produce plants wherein phenotypic characteristics are related to the presence of more than one chimeric gene.

The particular embodiments of this invention are further exemplified in the Examples. However, those skilled in the art will readily appreciate that the specific experiments detailed are only illustrative of the invention as described more fully in the claims which follow thereafter.

EXAMPLE 1

Isolation and Cloning of a Fungal Palmitoyl-COA Δ-9 Desaturase

Total RNA was isolated from 1.1 g of fresh *Aspergillus nidulans* cells by freezing and grinding said cells in a mortar and pestle which were pre-chilled with liquid $N_2$. Before grinding, a small amount of glass beads (150–212$\mu$M; SIGMA Chemical Company, St. Louis, Mo.) was added. The resulting powder was transferred to a centrifuge tube containing 10 mL liquidified phenol equilibrated with 0.1 M Tris-HCl, pH 8.0 and vortexed for 1 min. Organic and aqueous phases were separated by centrifugation at 4° C. and the aqueous phase was transferred to a fresh tube, extracted three times with phenol/chloroform/isoamyl alcohol (25:24:1 v/v/v) and once with chloroform/isoamyl alcohol (24:1 v/v). Nucleic acids were precipitated by adding 0.8 volume isopropanol, incubated at −20° C. for 1 h, followed by collection by centrifugation. The resulting pellet was resuspended in 5 mL DEPC-$H_2O$ ($H_2O$ having 0.1% v/v diethylpyrocarbonate). RNA was precipitated by adding 3 mL of 8.0 M LiCl followed by incubation on ice for 1 h. Precipitates were collected by centrifugation, resuspended in 5 mL DEPC-$H_2O$ and LiCl precipitated again. The final RNA pellet was resuspended in 500 $\mu$L DEPC-$H_2O$ and yield was determined by $A_{260\ nm}$. RNA purity and quality was confirmed by electrophoresis on agarose gel.

PolyA$^+$ RNA was purified on oligo dT-cellulose (Collaborative Biomedical Products, Bedford, Mass.) columns. Type 3 oligo-dT cellulose (0.1 g) was equilibrated in 5 mL of buffer 1 for 30 min, wherein buffer 1 was loading buffer with 0.5 M NaCl and loading buffer was 20 mM Tris-HCl, pH 7.6, 1 mM ethylenediaminetetraacetic acid (EDTA), and 0.1% sodium lauryl sulfate (SDS). The poured column was washed with 3 volumes of DEPC-H$_2$O, 3 volumes of wash buffer [0.1 N NaOH, 5 mM EDTA], 3 volumes of DEPC-H$_2$O, and 5 volumes of buffer 1. One mg of *Aspergillus nidulins* total RNA was heated at 65° C. for 5 min, diluted 2× with buffer 2 [2× loading buffer] and then applied to the oligo-dT column. The flow through material was collected, reheated, and reapplied to the column. The column was then washed with 10 volumes of buffer 1 followed by 10 volumes of buffer 3 [loading buffer having 0.1 M NaCl]. PolyA$^+$ RNA was eluted with 3 volumes of elution buffer [10 mM Tris-HCl, pH 7.5, 1 mM EDTA, 0.05% SDS] and collected in 0.5 mL fractions. RNA fractions were combined, buffered to 0.3 M sodium acetate pH 5.2, and precipitated at −20° C. for 16 h after addition of 2.2 volumes of 100% ethanol. The precipitate was collected by centrifugation, washed with 70% ethanol, dried, and dissolved in 50 μL DEPC-H$_2$O. This material was then repurified on a fresh oligo-dT column as described herein to produce highly-enriched polyA$^+$ mRNA.

Three μg polyA$^+$ mRNA was converted to cDNA and cloned into the LAMBDA UNI-ZAP vector, using the LAMBDA ZAP cDNA synthesis and cloning kit according to the manufacturers protocols (Stratagene, La Jolla, Calif.). The library had an original titer of 7.0×10$^5$ pfu/mL. The library was amplified according to Sambrook et al. (Molecular Cloning, A Laboratory Manual, 2nd Ed. (1989), Cold Spring Harbor Laboratory Press) and had a titer of 3.5×10$^{10}$ pfu/mL. The quality of the library was determined by analysis of individual clones. Clones had inserts ranging in size from 0.85 to 1.6 kb.

Total library cDNA was batch rescued and isolated as follows: 5 mL of XL1 Blue MRF' *E. coli* cells (Stratagene), at OD$_{600\ nm}$=1.0 in 10 mM MgSO4, were mixed with 1 μL (3.5×10$^7$ pfu) of amplified library phage stock, 10 μL (1.0×10$^8$ pfu) ExAssist helper phage (Stratagene), and incubated at 37° C. for 15 min. The mixture was added to 20 mL Luria-Bertani (LB) broth [10 g/L Tryptone, 5 g/L yeast extract, 10 g/L NaCl] and incubated at 37° C. for 3.5 h. The cells were heat killed by incubation at 68° C. for 0.5 h and cell debris was removed by centrifugation. One hundred μL of *E. coli* SOLR cells (Stratagene) at OD$_{600\ nm}$=1.0 in 10 mM MgSO$_4$ were mixed with 1.0 mL supernatant and incubated at 37° C. for 15 min. The mixture was used to inoculate 100 mL of Terrific Broth (TB) [12 g/L Tryptone, 24 g/L yeast extract, 4 mL/L glycerol, 17 mM KH$_2$PO$_4$, 72 mM KHPO$_4$] containing Ampicillin at 100 μg/mL. After overnight growth at 37° C. plasmid DNA was prepared using alkaline lysis/CsCl purification according to Sambrook et al. (Molecular Cloning, A Laboratory Manual, 2nd Ed. (1989), Cold Spring Harbor Laboratory Press). Yield of batch rescued cDNA was determined by A$_{260\ nm}$.

To isolate a clone encoding an Aspergillus palmitoyl-CoA Δ-9 desaturase, a DNA fragment was amplified using polymerase chain reaction technology, hereinafter PCR, to produce a probe which could be used to isolate a full length cDNA. A 5' primer and a 3' primer entered herein as SEQ ID NO:1 and SEQ ID NO:2, respectively, were synthesized on an Applied Biosystems High-Throughput DNA Synthesizer Model 394 (Foster City, Calif.). Batch-rescued maize embryo cDNA was used as template. PCR amplification was performed as follows: 200 ng template DNA, 10 μL 10× reaction buffer, hereinafter 10× RB, [100 mM Tris.HCl pH 8.3, 500 mM KCl, 15 mM MgCl2, 0.01% (w/v) gelatin], 10 μL of 2 mM deoxyribose nucleotides triphosphate (dNTPs), 3000 pmol primers (SEQ ID NO:1 and SEQ ID NO:2), 2.5 units AMPLITAQ DNA Polymerase (Perkin-Elmer, Norwalk, Conn.) and H$_2$O for a total volumne of 100 μL. A DNA Thermal Cycler (Perkin-Elmer Cetus Model #480) was programmed as follows: 96° C. for 1 min; [94° C. (30 sec), 37° C. (30 sec), 72° C. (2 min)] ×40 cycles; followed by a 7 min (72° C.) extension. A DNA product of 119 bp was obtained, sequenced as described below, and entered herein as SEQ ID NO:3. The DNA (SEQ ID NO:3) was cloned into the pCRI1 vector (Invitrogen, Carlsbad, Calif.) after gel purification on a 1% preparative SEAKEM GTG agarose gel (FMC, Rockland, Me.) in TAE [0.04 M Tris-acetate pH 8.1, 0.002 M EDTA]. DNA was extracted from agarose using GenElute Agarose Spin Columns (Supelco Inc., Bellefonte, Pa.) according to the manufacturer. Ligations and transformations were performed using the Original TA Cloning Kit (Invitrogen). Transformations were plated on LB-agar plates containing 25 μg/mL kanamycin and 50 μg/mL 5-bromo-4-chloro-3-indolyl-beta-D-galactopyranoside, hereinafter X-gal and allowed to grow overnight at 37° C. White colonies were isolated and grown in 2 mL of LB broth with 25 μg/mL kanamycin and plasmid DNA was extracted using alkaline lysis minipreps according to Sambrook et al. (Molecular Cloning, A Laboratory Manual, 2nd Ed. (1989), Cold Spring Harbor Laboratory Press). Plasmids containing the gene of interest were selected using restriction digest with EcoR1 to screen for an insert of about 120 bp.

Recombinant clones were sequenced by dideoxy chain termination using PRISM AMPLITAQ READY REACTION DYEDEOXY Terminator cycle sequencing kit #401384 according to the manufacturer (Perkin-Elmer Applied Biosystems Division, Foster City, Calif.). Samples were run on an ABI373A automated DNA sequencer (Perkin-Elmer, Applied Biosystems Division). DNA sequence analysis of SEQ ID NO:3 was performed using MACVECTOR v. 4.1.4 (Oxford Molecular, Campbell, Ky.), which gave theoretical translation thus generating the amino acid sequence entered herein as SEQ ID NO:4. The first six and last six amino acids of SEQ ID NO:4 correspond to the translational products of the PCR primers SEQ ID NO:1 and SEQ ID NO:2. The remaining amino acid sequence corresponded to a putative partial desaturase sequence from *Aspergillus nidulans*.

The DNA fragment corresponding to SEQ ID NO:3 was cut out of the vector by digestion with EcoR1 and purified using GenElute Agarose Spin Columns (Supelco). An [α$^{32}$P]-deoxyribocytosine triphosphate (dCTP)-labeled probe was generated using HIGHPRIME Random Labeling kit (Boehringer Mannheim, Indianapolis, Ind.) according to the manufacturer using 5 μL of [α$^{32}$P]-dCTP (3000 Ci/mmole, 10 μCi/μL, DuPont, NEN Life Science Products, Boston, Mass.). The labeled probe was purified over Nuc-Trap push columns (Stratagene) according to the manufacturer's procedures. Methods for phage titering, plating, coring and rescuing were performed in the LAMBDA ZAP II Library (Stratagene) instruction manual and were used herein. The cDNA library described herein was plated (50,000 pfu/plate) on four 24.3×24.3 cm NUNC assay plates (Nunc Inc. Roskilde, Denmark). Duplicate phage lifts were taken from each plate using 0.45 μm MAGNAGRAPH-NT nylon membrane (MSI, Westborough, Mass.). Filters were treated as follows: 5 min with 0.5 N NaOH/1.5 M NaCl, pH 12.8; 5 min air dry; 5 min with 0.5 M Tris, pH 7.6/1.5 M NaCl; and 5 min air dry. DNA was cross-linked to the membranes while on filter paper dampened with 2×SSC [1×SSC is 0.15 M NaCl, 0.015 M sodium citrate, pH 7.0] using a STRATALINKER UV Crosslinker (Stratagene). Filter prehybridization was performed at 42° C. in 150 mL hybridization buffer containing 50% (v/v) formamide, 6×SSC, 10×Denhardt's solution [1×Denhardt's solution is 0.02% Ficoll (Type 400, Pharmacia), 0.02% polyvinylpyrollidone, and 0.02% bovine serum albumin], 0.1% (w/v) SDS, and 200 µg/mL sheared and denatured salmon sperm DNA. After 3 h, used hybridization buffer was replaced with 100 mL of fresh hybridization buffer containing labeled probe having a specific activity=$5 \times 10^8$ dpm/µg. Hybridization continued for 18–20 h at 42° C. with gentle rotation. Afterwards, filters were washed twice at 55–60° C. for 40 min in 1 L of wash solution containing 0.2×SSc and 0.1% SDS. Filters were then exposed to Kodak XOMAT-AR Film (Eastman Kodak Company, Rochester, N.Y.) with intensifying screens (Lightening Plus, DuPont CRONEX, DuPont, Wilmington Del.) for 16 h at –70° C. Examination of films allowed the identification of positive plaques. Positive plaques were cored out and stored in 1 mL SM buffer [5.8 g/L NaCl, 2 g/L MgSO4, 20 mM Tris.HCl, pH 7.5, 5 mL/L of 2% (w/v) gelatin] with 50 µL chloroform. Phage were plated for secondary screening using 50 µL of a 1:1000 dilution of the primary phage stock. Positive plaques from the secondary screening were cored out and stored in 500 µL of SM buffer. Positive phage were then plated for tertiary screenings using amounts ranging from 5 µL of undiluted secondary stock to 20 µL of 1:100 dilution in SM buffer. All subsequent hybridizations were performed as described above. Isolates were rescued into phagemid form according to the LAMBDA-ZAP II Library Instruction Manual (Stratagene). Rescued phagemid were plated by combining 200 µL SOLR cells (Stratagene) grown to $OD_{600\ nm}$=0.5 to 1.0 with 50 to 100 µL phagemid and incubating for 15 min at 37° C. Cells containing phagemid were streaked on LB agar containing Ampicillin (75 µg/mL) and grown overnight at 37° C. DNA was extracted from 2 mL liquid cultures grown overnight at 37° C. in LB medium containing 100 µg/mL ampicillin. DNA was isolated by alkaline lysis minipreps, digested with EcoR1 and Xho1, and fractionated on 1.0% agarose gels. The DNA was transferred from the gel to Hybond N nylon membrane (Amersham Corporation, Arlington Heights, Ill.). Clones containing inserts with homology to the 119 bp desaturase probe were identified by hybridization using the ECL direct nucleic acid labeling and detection system (Amersham) according to the manufacturer's instructions. Clones hybridizing with the probe had inserts ranging in size from 0.7 to 1.6 kb.

Miniprep DNA from the positive clones was transformed into *E. coli* DH5α (Gibco-BRL Life Technologies, Bethesda, Md.), streaked for single colonies, and plasmid DNA was prepared by the alkaline lysis/CsCl procedure according to Sambrook et al. (Molecular Cloning, A Laboratory Manual, 2nd Ed. (1989), Cold Spring Harbor Laboratory Press). Plasmid was sequenced with primers located in the vector flanking the insert and primers based on the sequence of the internal PCR fragment. A second round of primers was designed based on the sequence obtained from the first round of sequencing. Sequencing was performed as described, supra., compiled, aligned and edited.with the SEQED program (Perkin-Elmer, Applied Biosystems Division). The resulting DNA sequence was entered herein as SEQ ID NO:5. DNA sequence analysis of SEQ ID NO:5 was performed using MACVECTOR v. 4.1.4 (Oxford Molecular, Campbell, Ky.), which gave theoretical translation thus generating the amino acid sequence entered herein as SEQ ID NO:6.

EXAMPLE 2

Construction of Plant Transformation Vectors

In order to express the Aspergillus desaturase in maize in a constitutive manner, the open reading encoded by SEQ ID NO:5 was cloned in plasmid pDAB439 between the ubiquitin promoter/intron and Nos terminator, thus making pDAB463. Plasmid pDAB439 was a 7040 base pairs double stranded plant transformation vector composed of the following sequences in clockwise order. The plasmid backbone was derived from pUC19 (Yanish-Perron et al., (1985) Gene 33:103–119). Nucleotides 1 to 2252 of pDAB439 corresponded to the reverse complement of nucleotides 435 to 2686 of pUC19. Nucleotides 2253 to 2271 of pDAB439 had the sequence TGCATGTGTT CTCCTTTTT. Nucleotides 2272 to 4264 of pDAB439 were the maize ubiquitin promoter and first intron, and were PCR amplified from genomic DNA of maize genotype B73 (Christensen et al., (1992) Plant Mol. Biol. 18:675–689). Nucleotides 4265 to 4308 of pDAB439 had the sequence GGTACGGCCATAT-TGGCCGA GCTCGGCCTC TCTGGCCGAT CCCC. Nucleotides 4309 to 4576 of pDAB439 corresponded to nucleotides 4420 to 4687 of plasmid pBI101 (Clontech, Palo Alto, Calif.) followed by the linker GG as nucleotides 4577 and 4578 of pDAB439. Nucleotides 4579 to 4743 of pDAB439 were the reverse complement of nucleotides 238–402 of pUC19. Nucleotides 4744 to 4807 of pDAB439 corresponded to: GCGGCCGCTT TAACGCCCGG GCATTTAAAT GGCGCGCCGC GATCGCTTGC AGATCTGCAT GGG. Nucleotides 4808–5416 of pDAB439 comprised the double enhanced 35S promoter, with nucleotides 5070 to 5416 corresponding to nucleotides 7093 to 7439 of the Cauliflower Mosaic Virus genome (Franck et al., (1980) Cell 21:285–294). Nucleotides 4808 to 5061 of pDAB439 were a duplication of nucleotides 5068 to 5321. Nucleotides 5062 to 5067 of pDAB439 comprised the linker CATCGA. Nucleotides 5417–5436 of pDAB439 comprised the linker GGGGACTCTA GAGGATCCAG. Nucleotides 5437 to 5547 of pDAB439 corresponded to nucleotides 167 to 277 of the Maize Streak Virus genome (Mullineaux et al., (1984) EMBO J. 3:3063–3068). Nucleotides 5548 to 5764 of pDAB439 corresponded to the modified first intron of the maize alcohol dehydrogenase gene (Adh1-S) (Dennis et al., (1984) Nucleic Acids Res. 12:3983–4000). The modification resulted in removal of 343 nucleotides (bases 1313 to 1656) with bases 1222 to 1312 (intron 5' end) and nucleotides 1657 to 1775 (intron 3' end) of the maize Adh1-S gene remaining. Nucleotides 5765 to 5802 of pDAB439 corresponded to Maize Streak Virus (MSV) nucleotides 278 to 312, followed by the linker sequence CAG. Both sections of the Maize Streak Virus, hereinafter MSV, sequence comprised the untranslated leader of the MSV coat protein V2 gene, and were interrupted in plasmid pDAB439 by the modified Adh1 intron. Nucleotides 5803 to 6359 of plasmid pDAB439 corresponded to nucleotides 29 to 585 of the phosphinotricin acetyl transferase (BAR) gene of Streptomyces hygroscopicus (White et al., (1989) Nucleic Acids Res. 18:1062). To facilitate cloning, nucleotides 34 and 575 of the published sequence were changed from A and G to G and A, respectively. This sequence served as the selectable marker in plant cells. Nucleotides 6360 to 6364 comprised the linker GATCT. Nucleotides 6365 to 6635 of pDAB439 corresponded to nucleotides 4420 to 4683 of plasmid pBI101 (Clontech, Palo Alto, Calif.) followed by the linker sequence AGATCGC. Nucleotides 6636 to 6639 of pDAB439 comprised the linker TCGG. The remaining sequence of pDAB439 (nucleotides 6640 to 7040) corresponded to nucleotides 284 to 684 of pUCl9.

SEQ ID NO:5 was modified so that it could be placed into plasmid pDAB439. To this end SEQ ID NO:5 was amplified with primers as disclosed herein in SEQ ID NO:7 and SEQ ID NO:8. Amplification was performed in six simultaneous reactions as follows: 200 ng template DNA (SEQ ID NO:5), 10 μL 10× RB, 10 μL of 2 mM dNTPs, 3000 pmol primers (SEQ ID NO:7 and SEQ ID NO:8), 2.5 units AMPLITAQ DNA Polymerase (Perkin-Elmer, Norwalk, Conn.) and water (total volume=100 μL). A DNA Thermal Cycler (Perkin-Elmer Cetus Model #480) was programmed as follows: 96° C. for 1 min; [94° C. (30 sec), 72° C. (2 min)] for 15 cycles; followed by a 7 min (72° C.) extension. Following amplification, reactions were pooled, the DNA was precipitated with ethanol, and the pellet was resuspended in 40 μL TE buffer [10 mM Tris.HCl pH 8.0, 1 mM EDTA]. Twenty μL DNA was digested with 60 units Sfi1 in 60 μL volume, electrophoresed on a preparative 1% agarose gel, and the liberated 1.4 kbp fragment was isolated from the gel using GenElute columns. The purified DNA was ethanol precipitated and the pellet was resuspended in 20 μL TE buffer. Two μL of fragment were ligated into 100 ng pDAB439 which had been digested with Sfi1. Ligations, transformation, and analysis of recombinant clones was done according Sambrook et al. A clone containing the 1.4 kbp insert was selected and sequenced. The sequence of the insert was identical to nucleotides 4–1371 of SEQ ID NO:5, with exception being the changes that were introduced deliberately, to improve the translation context around the ATG codon. This plasmid was named pDAB463.

In order to express the Aspergillus desaturase in maize in a seed specific manner, the ubiquitin promoter/intron in pDAB463 were replaced by the promoter of the maize globulin gene. The globulin promoter was amplified from maize genomic DNA and cloned in plasmid pGGN62-2. Plasmid pGGN62-2 was a 6321 base pair plasmid comprised of the following: nucleotides 1 to 1257 corresponded to nucleotides 4 to 1260 of SEQ ID NO:9; nucleotides 1258 to 3399 corresponded to bases 898 to 3039 of pBI221 (Clontech) in which eight bases of the β-glucuronidase gene, hereinafter GUS gene, were reengineered to contain an Nco1 site at the ATG start codon to facilitate cloning and maintain sequences optimal for translation initiation. This resulted in the first eight base pairs of the GUS gene having the sequence CCATGGTC resulting in an amino acid sequence change from Met Leu to Met Val. The remaining nucleotides in pGGN62-2 (3400 to 6321) corresponded to nucleotides 1 to 2916 of pBLUESCRIPT SK– (Stratagene) with nucleotide 1 being defined as the first A residue of the unique Hind3 site and proceeding clockwise towards the Xho1 site. The six base difference in the number of bases was due to base deletions in the published sequence from 232 to 235 and 663 to 664.

In order to subclone the globulin promoter into plasmid pDAB463, a unique Pac1 site was created upstream of the globulin promoter in plasmid pGGN62-2. An Xba1 to Pac1 adapter having the sequence CTAGCTTAAT TAAG was phosphorylated with ATP and T4 polynucleotide kinase, annealed and ligated into pGGN62-2 which had been digested with Xba1 and treated with Calf Intestinal Phosphatase according to Sambrook et al. Clones containing the adapter were screened by digestion of minipreps with Pac1, and one clone which was cut by Pac1 and not by Xba1 was named pGGN62-2Pl. The globulin promoter fragment was cut out by digestion with Pac1 and Nco1, purified by preparative gel electrophoresis, and GenElute columns. Plasmid pDAB463 was cut to completion with Pac1, and a partial digestion was performed with Nco1. The linear fragment of 6.4 kbp was purified by preparative gel electrophoresis and GenElute columns, and following ethanol precipitation was ligated to the globulin promoter fragment.

Clones having the globulin promoter upstream of the Aspergillus desaturase were screened by digestion of miniprep DNAs with NcoI. One plasmid having the correct digestion pattern, was named pDAB470 and was sequenced across the cloning junction to verify that sequences around the ATG codon had not been altered.

The Aspergillus desaturase was also be used to modify lipid composition of dicot species. In order to express the gene in a seed specific manner, the Aspergillus desaturase was placed behind the phaseolin promoter from *Phaseolus vulgaris*. This promoter has been extensively characterized and was shown suitable for high level, seed specific, expression in tobacco. The phaseolin promoter/Aspergillus desaturase gene were placed into is plasmid phaGN184-2.

Plasmid phaGN184-2 was constructed as follows. The maize expression vector, phaGN184-2, containing the 5' regulatory element from the β-phaseolin gene of *Phaseolus vulgaris* driving the β-glucuronidase gene was used in the expression studies. Plasmid phaGN184-2 was a 6657 base pairs double stranded plant transformation vector composed of the following sequences in clockwise order. Nucleotides 1 to 64 had the polylinker sequence from several subclonings and included the sequence CCACCGCGGT GGCGGCCGCT CTAGATGCAT GCTCGAGCGG CCGCCAGTGT GATGGATATC TGCA. Nucleotides 65 through 1611 contained the 5' regulatory sequences from the P-phaseolin gene of *Phaseolus vulgaris* as disclosed in SEQ ID NO:10. Base 1113 of phaGN184-2 (which corresponded to base 1049 of SEQ ID NO:10) was modified from a C to a T to facilitate subsequent cloning. Nucleotide 1612 of phaGN184-2 was a C. Nucleotides 1613 through 3464 corresponded to nucleotides 2551 to 4402 of plasmid pBI101 (Clontech, Palo Alto, Calif.). Bases 1613 to 3418 encoded the β-glucuronidase gene of Jefferson et al. (1987 EMBO J. 6:3901–3907) with bases 1616–1618 modified from TTA to GTC to facilitate cloning and maximize translation initiation. Bases 3465 through 3474 were composed of the linker sequence TGGGGAATTG. Bases 3475 through 3744 of phaGN184-2 were composed of 4414 through 4683 of pBI101 (Clontech, Palo Alto, Calif.). This sequence was followed by linker ATCGGGAATT corresponding to bases 3745 through 3754. The remaining sequence of phaGN184-2 (nucleotides 3755 to 6657) corresponded to reverse complement of nucleotides from the plasmid backbone which was derived from pUC19 (Yanish-Perron et al., (1985) Gene 33:103–119).

To facilitate transfer of the phaseolin promoter from this plasmid to pDAB463, a unique Xba1 site upstream of the phaseolin promoter was changed into a unique Pac1 site, using the adapter as described above. The resulting plasmid, phaGN184-2P1, was cut with Pac1 and Nco1. The liberated phaseolin promoter fragment was purified from gel and ligated into pDAB463, which had been digested to completion with Pac1, partially digested with Nco1 and purified as described above. The resulting plasmids were screened with Nco1, and two clones were identified which had the appropriate restriction pattern. One of these two clones was named pDAB471, and was sequenced across the phaseolin/desaturase junction to verify that no unintended changes had been made during the modification. The phaseolin/desaturase/nosA gene cassette was transferred to binary vector pDAB1542.

The plasmid pDAB1542 was constructed using standard molecular biology procedures. The 10323 base pair sequence is disclosed herein as SEQ ID NO:11. The starting position was the Hind III site (AAGCTT) which represented bases 602 to 607 of the T-DNA sequence of pTi-15955 from

*Agrobacterium tumefaciens* strain 15955, and which has NCBI Accession Number X00493 J05108 X00282. Nucleotides 1 to 579 of SEQ ID NO:11 represented bases 602 to 1184 of pTi-15955, except that the sequence GTAC, representing nucleotides 622–625 of pTi-15955, had been deleted to destroy a Kpn I recognition site. This sequence section included T-DNA Border A (bases 304 to 327). Nucleotides 580 to 597 of SEQ ID NO:11 were remnants of cloning manipulations. Nucleotides 598 to 2027 of SEQ ID NO:11 were derived from *Escherichia coli* transposon Tn903, and corresponded generally to bases 835 to 2264 of NCBI Accession Number J01839, with the following modifications: base 1467 of J01839 (C) was mutated to T (base 1230 of SEQ ID NO:11) to destroy a Sma I recognition site, and base 1714 of J01839 (C) was mutated to T (base 1477 of SEQ ID NO:11) to destroy a Hind III recognition site. Bases 925 to 1740 of SEQ ID NO:11 were an open reading frame encoding the neomycin phosphotransferase I protein from Tn903. Nucleotides 2028 to 2062 of SEQ ID NO:11 were remnants of cloning manipulations. Bases 2063 to 2080 of SEQ ID NO:11 was derived from *E. coli* transposon Tn5 (NCBI Accession Number U00004 L19385), and represented bases 2519 to 2536 of that sequence (complementary strand). Bases 2081 to 2793 of SEQ ID NO:11 represented nucleotides 21728 to 22440 of pTi-15955 (NCBI Accession Number X00493 J05108 X00282). Bases 2794 to 3772 of SEQ ID NO:1i were Tn5 bases 1540 to 2518 (complementary strand), with the following modifications; base 1532 of Tn5 (G) was mutated to T (base 3764 of SEQ ID NO:11 and base 1536 of Tn5 (C) was mutated to G (base 3768 of SEQ ID NO:11) to create a BamH I site. Bases 2967 to 3761 of SEQ ID NO:11 (complementary strand) were the open reading frame encoding the neomycin phosphotransferase II protein of Tn5. Nucleotides 3773 to 3784 of SEQ ID NO:11 were remnants of cloning manipulations. Bases 3785 to 4174 of SEQ ID NO:11 were bases 5376 to 5765 of NCBI Accession Number V00141 J02048, and composed the 19S promoter of the CabbS strain of Cauliflower Mosaic Virus. Bases 4175 to 4272 of SEQ ID NO:11 comprised a multiple cloning site for the introduction of heterologous DNA fragments into pDAB1542, and included unique restriction enzyme recognition sites for Bgl II (AGATCT), Asc I (GGCGCGCC), Swa I (ATTTAAAT), Srf I (GCCCGGGC), Pme I (GTTTAAAC), Not I (GCGGCCGC), and Pac I (TTAATTAA). Nucleotides 4273 to 4624 of SEQ ID NO:11 represented bases 13926 to 14277 of pTi-15955 (NCBI Accession Number X00493 J05108 X00282), and included the T-DNA Border B as bases 4407 to 4432, and the overdrive sequence as bases 4445 to 4468. Bases 4625 to 4630 were a Hind III recognition site (AAGCTT), which represents the junction between the modified T-DNA portion of pDAB1542 and the plasmid vector components.

Bases 4631 to 5433 of SEQ ID NO:11 were derived from plasmid pR29 (Morrisson, D. A., M.-C. Trombe, M.-K. Hayden, G. A Waszak, and J.-D. Chen, J. Bacteriol. 159:870–876, 1984); the sequence thereof has not been previously disclosed. They were obtained as part of an 1824 base pair Hind III/Ava I fragment containing the erythromycin resistance determinant from pR29. Bases 5434 to 5828 of SEQ ID NO:11 corresponded to nucleotides 1 to 395 of STRERMAM1 (NCBI Accession Number M20334). Bases 5534 to 6448 of SEQ ID NO:11 corresponded generally to EHERMAM (NCBI Acession Number X81655), with the following exceptions: Bases corresponding to nucleotides 5586, 5927, 5930,and 5931 (all G's) of SEQ ID NO:11 were reported as A residues in EHERMAM. In addition, bases 5933 (T), 5934 (T), 5935 1(C), 5936 (T), and 5938 (C) of SEQ ID NO:11 were A residues in EHERMAM. Nucleotides 5943 to 6448 of SEQ ID NO:11 corresponded to bases 1 to 506 of STRERMAM2 (NCBI Accession Number M20335), with bases 5546 to 6280 of SEQ ID NO:11 comprising an open reading frame encoding a putative adenine methylase protein.

Nucleotides 6448 to 8866 of SEQ ID NO:11 represented nucleotides 15435 to 17853 of plasmid RK2 (NCBI Accession Number L27758), with the following exceptions: The L27758 sequence included an additional T between bases 6573 and 6574 of SEQ ID NO:11, and an additional C between bases 6904 and 6905 of SEQ ID NO:11. . Also, bases 6651 (G), 7446 (A), 7461 (A), 7479 (A), and 7494 (T) of SEQ ID NO:11 were found as a C, a C, a C, a G, and a C in L27758. Nucleotides 8861 to 9602 of SEQ ID NO:11 represented bases 50632 to 51373 of L27758, and nucleotides 9614 to 10322 of SEQ ID NO:11 were the complementary strand of bases 12109 to 12817 of L277758, with the following exceptions: bases 9742 (T) and 10024 (C) of SEQ ID NO:11 were both A residues in L27758, and base 10191 (T) of SEQ ID NO:11 was not represented in the RK2 sequence of L27758. Bases 9603 to 9613, and bases 10323 of SEQ ID NO:11 were remnants of cloning manipulations.

Plasmid pDAB1542 was digested to completion with Pac1 and Asc1 and treated with Calf Intestinal Phosphatase. Plasmid pDAB471 was digested with Pac1 and Asc1, and the 3.4 kbp insert was purified by gel electrophoresis and GenElute columns, ethanol precipitated and resuspended in 20 μL TE buffer. Seven μL gel purified fragment was ligated to 200 ng pDAB1542 vector, and transformed into *E. coli* DH5α cells. Resulting colonies were screened for presence of the insert by digestion of miniprep DNAs with Pac1 and Asc1. One resulting clone having the desired restriction pattern was named pDAB473, and was used in subsequent tobacco transformations.

A control plasmid for tobacco transformation (pDAB1542) which containing a phaseolin/GUS/nosA cassette instead of phaseolin/desaturase/nosA, was constructed as follows. pDAB1542 was digested with Pac1 and Srf1, and treated with Calf Intestinal Phosphatase as described by Sambrook et al. Plasmid phaGN184-2P1 was digested with Pac1 and Pvu2, ethanol precipitated and resuspended in TE buffer. Approximately 1 μg digested phaGN184-2 was shotgun ligated to 200 ng vector and transformed into DH5α *E. coli* cells. Clones with inserts were selected by screening miniprep DNAs with Bgl II. Two clones with a 3.1 kbp Bgl II fragment, diagnostic of the presence of the phaseolin/ GUS/nosA gene cassette, were identified. One clone, named pDAB474, was used as a control in subsequent tobacco transformations.

EXAMPLE 3

Transformation of Tobacco with a Phaseolin/ Aspergillus Desaturase/Nos Construct and Control Plasmids The *E. coli* DH5α strains carrying plasmids pDAB473 and pDAB474, and an *E. coli* strain containing plasmid pRK2013 (Clontech), were grown to log phase in YEP media [10 g/L yeast extract, 10 g/L peptone, 5 g/L sodium chloride] containing 50 μg/L kanamycin. *Agrobacterium tumefaciens* strain EHA101S (deposited in Agricultural Research Service Culture Collection (NRRL) 1815 North University Street, Peoria, Ill. 61604; Deposit number XXX) was grown at 28° C. to log phase in YEP medium containing streptomycin at 250 μg/L. The cultures were centrifuged to pellet the cells, and each cell pellet was resuspended in 500 μL LB medium. For pDAB473 mating, 100 μL of E. coli DH5α/pDAB473 cell suspension was mixed with 100 μL of E. coli containing pRK2013 and 100 μL Agrobacterium EHA101S. The mixed suspension was plated on LB-agar plates, and incubated at 28° C. for 24 h. The cells were scraped of the plate and resuspended in 1 mL of LB medium, and serially diluted from $10^{-3}$ to $10^{-6}$ in sterile water. 100 μL of each dilution was plated on YEP agar plates, containing erythromycin at 100 μg/L and streptomycin at 250 μg/L, and were incubated at 28° C. for 2 days, until colonies were clearly visible. Ten colonies from the $10^{-5}$ dilution were streaked out for single colonies on the same medium twice, to ensure that Agrobacterium transconjugants were free from contaminating E. coli. For each transconjugant, a 4 mL over night culture was grown in YEP containing erythromycin and streptomycin, and plasmid DNA was prepared using the standard alkaline lysis miniprep procedure. Miniprep DNA was digested with EcoR1, and each transconjugant was shown to contain plasmid DNA having the expected restriction pattern. Conjugation of plasmid pDAB474 into Agrobacterium was done as described above for pDAB473.

EXAMPLE 4

Expression of Aspergillus Delta-9 in Tobacco

Tobacco transformation with Agrobacterium tumefaciens was carried out by a method similar to published methods (Horsch et al., 1988 Plant Molecular Biology Manual; Gelvin et al, eds., Kluwer Academic Publishers, Boston, Mass.). To provide source material for the transformation, tobacco seed (Nicotiana tabacum cv. Xanthi) were surface sterilized and planted on the surface of TOB-, which is a hormone-free Murashige and Skoog (MS) medium (Murashige and Skoog, 1962 Plant Physiol. 75:473–497) solidified with agar. Plants were grown for 6–8 weeks in a lighted incubator room at 28–30° C. and leaves were collected sterilely for use in the transformation protocol. Approximately 1 cm$^2$ pieces were sterilely cut excluding the midrib. Cultures of the Agrobacterium strains (EHA101S containing pDAB473 or pDAB474), which had been grown overnight on a rotor at 28° C., were pelleted in a centrifuge and resuspended in sterile MS salts and adjusted $OD_{600\ nm}$ =0.7. Leaf pieces were dipped therein for about 30 sec, then blotted dry on sterile paper towels and placed right side up on medium TOB+ (MS medium containing 1 mg/L indole acetic acid and 2.5 mg/L benzyladenine) and incubated in the dark at 28° C. Two days later the leaf pieces were moved to medium TOB+ containing 250 mg/L cefotaxime (Agri-Bio, North Miami, Fla.) and 100 mg/L kanamycin sulfate (AgriBio) and incubated at 28–30° C. in the light. Leaf pieces were moved to fresh TOB+ with cefotaxime and kanamycin twice per week for the first two weeks and once per week thereafter. Leaf pieces which showed re-growth of the Agrobacterium strain were moved to medium TOB+ with cefotaxime and kanamycin, plus 100 mg/L vancomycin HCl (Sigma). After four weeks, small plants arising from transformed foci were removed, planted onto medium TOB– containing 250 mg/L cefotaxime and 100 mg/L kanamycin, and grown in a lighted incubator room. After 3–4 weeks these plants had grown to a size sufficient that leaf samples could be analyzed for the presence of the transgene. Afterwards, plants were transplanted into soil in the greenhouse and held under standard greenhouse conditions (30° C., 16 H light) until mature, self-pollinated seed capsules had developed. Oil content of said seed capsules were then analyzed as described herein.

EXAMPLE 5

Analysis of the Fatty Acid Composition of Tobacco Seeds Transformed with Aspergillus Palmitoyl-CoA Δ-9 Desaturase The procedure for extraction and esterification of fatty acids from plant tissue was a modification of Browse et. al. ((1986) Anal. Biochem. 152:141–145). One to 20 mg of plant tissue was placed in a test tube. After addition of 1 mL of methanolic-HCL (Supelco, Bellefonte, Pa.), the tubes were purged with nitrogen gas and sealed. Tubes were then heated at 80° C. for 1 h and allowed to cool. Fatty acid methyl esters were removed from the reaction mixture by extraction with hexane, which involved adding 1 mL of hexane and 1 mL of 0.9% (w/v) NaCl followed by vigorous shaking. After centrifugation at 16,000×g for 5 min the top hexane layer was removed and used for FAME analysis. Analysis was performed by injection of 1 μL of sample on a Hewlett-Packard (Wilmington, Del.) Series II model 5890 gas chromatograph equipped with a flame ionization detector and a J&W Scientific (Folsom, Calif.) DB-23 column. The oven temperature was maintained at 150° C. throughout the run (20 min) and the flow of the carrier gas (helium) was 80 cm/sec. Conditions allowed separation of the six fatty acid methyl esters of interest having varying carbon lengths: 16:0, palmityl methyl ester; 16:1, palmitoyl methyl ester; 18:0, stearyl methyl ester; 18:1, oleoyl methyl ester; 18:2, linoleoyl methyl ester; and 18:3, linolenyl methyl ester. Data collection and analysis was performed with a Hewlett-Packard Series II Model 3396 integrator and a PE Nelson (Perkin-Elmer) data collection system. The percentage of each fatty acid methyl ester in the sample was taken directly as indicated by the data collection system. Quantitative amounts of each fatty acid methyl ester were calculated using peak areas of a standard (Matreya, Pleasant Gap, Pa.) having known amounts of the five fatty acid methyl esters of interest. The amount determined was used to estimate the percentage of each fatty acid per total fresh weight. Adjustments were not made for loss of fatty acids during the extraction and esterification procedure since recoveries typically ranged from 90 to 100% depending on the original amount of the sample. The presence of plant tissue in the extraction mixture had no effect on the recovery of known quantities of standard.

Transgenic tobacco seeds produced as described herein were analyzed at maturity. From each independent plant three seed cases were harvested. Fatty acid methyl esters were extracted from 20 mg seeds for each sample as described above. The data are summarized in Table 3.

TABLE 3

Fatty acid composition and percent of lipids per fresh weight of tobacco seeds from plants transformed with pDAB473 (Aspergillus desaturase construct) and pDAB474 (control construct).

| Line | % 16:0 | % 18:0 | % 16:1 | % 18:1 | % 18:2 | % 18:3 | % FW Lipid |
|---|---|---|---|---|---|---|---|
| 473.6 | 6.99 | 1.33 | 4.65 | 13.89 | 71.28 | 0.98 | 17.33 |
|  | ± | ± | ± | ± | ± | ± | ± |
|  | 0.31 | 0.14 | 0.21 | 0.67 | 0.20 | 0.07 | 1.35 |
| 473.8 | 7.10 | 0.83 | 4.07 | 12.52 | 73.80 | 0.94 | 13.11 |
|  | ± | ± | ± | ± | ± | ± | ± |
|  | 0.21 | 0.10 | 0.07 | 0.91 | 1.25 | 0.01 | 2.80 |
| 473 avg | 8.52 | 1.27 | 3.01 | 13.21 | 72.25 | 1.03 | 16.08 |
|  | ± | ± | ± | ± | ± | ± | ± |
|  | 1.15 | 0.33 | 1.17 | 1.69 | 2.05 | 0.14 | 3.95 |

TABLE 3-continued

Fatty acid composition and percent of lipids per fresh weight of tobacco seeds from plants transformed with pDAB473 (*Aspergillus desaturase* construct) and pDAB474 (control construct).

| Line | % 16:0 | % 18:0 | % 16:1 | % 18:1 | % 18:2 | % 18:3 | % FW Lipid |
|---|---|---|---|---|---|---|---|
| 474 avg | 10.09 ± 0.42 | 2.42 ± 0.27 | 0.22 ± 0.03 | 13.17 ± 1.44 | 72.88 ± 1.20 | 0.81 ± 0.07 | 24.04 ± 8.98 |

Transformation of tobacco with pDAB473, containing the Aspergillus palmitoyl-CoA Δ-9 desaturase gene expressed under control of the phaseolin promoter led to dramatic changes in the tobacco seed fatty acid composition, when compared to controls (pDAB474). Palmitoleic acid (16:1Δ9), which is normally present in only minute amounts, accumulated to about 4.0%. As a result the amount of saturated fatty acids was decreased, and both palmitic acid (16:0) and stearic acid (18:0) were affected.

EXAMPLE 6

Production and Regeneration of Transgenic Aspergillus Δ-9 Desaturase Maize Isolates Type II callus cultures were initiated from immature zygotic embryos of the genotype "Hi-II." (Armstrong et al, (1991) Maize Cooperation Newsletter, pp.92–93). Embryos were isolated from greenhouse-grown ears from crosses between Hi-II parent A and Hi-II parent B or F2 embryos derived from a self- or sib-pollination of a Hi-II plant. Immature embryos (1.5 to 3.5 mm) were cultured on initiation medium consisting of N6 salts and vitamins (Chu et al, (1978) The N6 medium and its application to anther culture of cereal crops. Proc. Symp. Plant Tissue Culture, Peking Press, 43–56) 1.0 mg/L 2,4-D, 25 mM L-proline, 100 mg/L casein hydrolysate, 10 mg/L AgNO$_3$, 2.5 g/L GELRITE, and 20 g/L sucrose, with a pH of 5.8. Selection for Type II callus took place for ca. 2–12 weeks. After four to six weeks callus was subcultured onto maintenance medium (initiation medium in which AgNO$_3$ was omitted and L-proline was reduced to 6 mM).

The plasmids pDAB463 and pDAB470 were transformed into embryogenic callus via helium bombardment. For blasting 140 μg of plasmid DNA was precipitated onto 60 mg of alcohol-rinsed, spherical gold particles (1.5–3.0 μm diameter) by adding 74 μL of 2.5 M CaCl$_2$H$_2$O and 30 μL of 0.1 M spermidine (free base) to 300 μL of plasmid DNA and H$_2$O. The solution was immediately vortexed and the DNA-coated gold particles were allowed to settle. The resulting clear supernatant was removed and the gold particles were resuspended in 1 ml of absolute ethanol. This suspension was diluted with absolute ethanol to obtain 15 mg DNA-coated gold/mL.

Approximately 600 mg of embryogenic callus tissue was spread over the surface of Type II callus maintenance medium as described herein lacking casein hydrolysate and L-proline, but supplemented with 0.2 M sorbitol and 0.2 M mannitol as an osmoticum. Following a 4 h pre-treatment, tissue was transferred to culture dishes containing blasting medium (osmotic media solidified with 20 g/L tissue culture agar (JRH Biosciences, Lenexa, Kans.) instead of 7 g/L GELRITE (Schweizerhall, South Plainfield, N.J.). Helium blasting accelerated suspended DNA-coated gold particles towards and into the prepared tissue targets. The device used was an earlier prototype of that described in U.S. Pat. No. #5,141,131 which is incorporated herein by reference. Tissues were covered with a stainless steel screen (104 μm openings) and placed under a partial vacuum of 25 inches of Hg in the device chamber. The DNA-coated gold particles were further diluted 1:1 with absolute ethanol prior to blasting and were accelerated at the callus targets four times using a helium pressure of 1500 psi, with each blast delivering 20 μL of the DNA/gold suspension. Immediately post-blasting, tissue was transferred to osmotic media for a 16–24 h recovery period. Afterwards, the tissue was divided into small pieces and transferred to selection medium (maintenance medium lacking casein hydrolysate and L-proline but having 30 mg/L BASTA (Agrevo)). Every four weeks for 3 months, tissue pieces were non-selectively transferred to fresh selection medium. After 7 weeks and up to 22 weeks, callus sectors found proliferating against a background of growth-inhibited tissue were removed and isolated. The resulting BASTA-resistant tissue was subcultured biweekly onto fresh selection medium. Following gas chromatography/fatty acid methyl ester, hereinafter GC/FAME, analyses, as described herein, positive transgenic lines were identified and transferred to regeneration media.

Regeneration was initiated by transferring callus tissue to cytokinin-based induction medium, which consisted of Murashige and Skoog salts, hereinafter MS salts, and vitamins (Murashige and Skoog, (1962) Physiol. Plant. 15: 473–497) 30 g/L sucrose, 100 mg/L myo-inositol, 30 g/L mannitol, 5 mg/L 6-benzylaminopurine, hereinafter BAP, 0.025 mg/L 2,4-D, 30 mg/L BASTA, and 2.5 g/L GELRITE (Schweizerhall) at pH 5.7. The cultures were placed in low light (125 ft-candles) for one week followed by one week in high light (325 ft-candles). Following a two week induction period, tissue was non-selectively transferred to hormone-free regeneration medium, which was identical to the induction medium except that it lacked 2,4-D and BAP, and was kept in high light. Small (1.5–3 cm) plantlets were removed and placed in 150×25 mm culture tubes containing SH medium (SH salts and vitamins (Schenk and Hildebrandt, (1972) Can. J. Bot. 50:199–204), 10 g/L sucrose, 100 mg/L myo-inositol, 5 mL/L FeEDTA, and 2.5 g/L GELRITE (Schweizerhall), pH 5.8). Plantlets were then transferred to 10 cm pots containing approximately 0.1 kg of METRO-MIX 360 (The Scotts Co. Marysville, Ohio) in the greenhouse as soon as they exhibited growth and developed a sufficient root system. They were grown with a 16 h photoperiod supplemented by a combination of high pressure sodium and metal halide lamps, and were watered as needed with a combination of three independent Peters Excel fertilizer formulations (Grace-Sierra Horticultural Products Company, Milpitas, Calif.). At the 3–5 leaf stage, plants were transferred to five gallon pots containing approximately 4 kg METRO-MIX 360.

Primary regenerants were self- or sib-pollinated, or outcrossed to either elite inbreds or transgenic plants after an additional 6–10 weeks in the 5 gallon pots. $R_1$ seed was collected at 40–45 days post-pollination.

EXAMPLE 7

Method for Production of Maize Somatic Embryos and Analysis of Fatty Acids Therein Embryogenic callus material containing the genes of interest was maintained as described herein. Continuous production of somatic embryos, which made up a large portion of embryogenic callus, was performed by transferring the callus tissue every two weeks. While the somatic embryos continued to proliferate, they usually remained in an early stage of embryo development because of the continued presence of 2,4-D in the culture medium. Somatic embryos could be regenerated into plantlets when callus was subjected to the regeneration procedure described herein. During regeneration, somatic embryos formed roots and a shoot, subsequently ceasing development as an embryo.

Somatic embryos were made to develop as seed embryos by growing embryogenic callus on MS medium containing 6% (w/v) sucrose. The callus was grown for 7 days and then somatic embryos were individually transferred to MS medium with 6% sucrose and 10 μM abscisic acid, hereinafter ABA.

Somatic embryos were assayed for fatty acid composition using GC/FAME 3 to 7 days after growth on MS medium containing 6% sucrose and 10 μM ABA. Their fatty acid composition was compared to the fatty acid composition of embryogenic callus and to maize zygotic embryos 12 DAP (Table 4). Fatty acid composition of embryogenic callus differed from that of somatic embryos in that the callus had higher percentages of 16:0 and 18:3 while having lower percentages of 18:1 and 18:2. In addition, the percentage of lipid by fresh weight for the embryogenic callus was 0.4% compared to the somatic embryos 4.0%. The fatty acid composition of the zygotic embryos and somatic embryos were very similar and their percentage of lipid by fresh weight were nearly identical. These data validated the use of the somatic embryo culture system as an in vitro system for testing the effect of certain genes on lipid synthesis in developing embryos of maize.

Somatic embryos transformed with pDAB463 and pDAB470 were produced from embryogenic callus using the methods described herein. Control somatic embryos were produced from untransformed lines having backgrounds identical to that of the transformed lines. For the lines tested, 16:1Δ9 was detected in somatic embryos with the highest level being was about 2.7%. Detection of 16:1Δ9 was rare in the control lines, and when it was detected, the levels were never higher than about 0.2% in a single embryo. Table 5 shows the total fatty acid composition of somatic embryos produced from lines 463-09 and 463-43, in which 16:1Δ9 averaged about 0.4% and about 1.2% respectively.

TABLE 4

A comparison of the fatty acid composition of embryogenic callus, somatic embryos and zygotic embryos.

| Fatty Acid Methyl Ester | Percent Fatty Acid Composition | | |
|---|---|---|---|
| | Embryogenic Callus[a] | Somatic Embryo[ab] | Zygotic Embryo[ac] |
| 16:0 | 19.4 ± 0.9 | 12.6 ± 0.7 | 14.5 ± 0.4 |
| 18:0 | 1.1 ± 0.1 | 1.6 ± 0.8 | 1.1 ± 0.1 |
| 18:1 | 6.2 ± 2.0 | 18.2 ± 4.9 | 18.5 ± 1.0 |
| 18:2 | 55.7 ± 3.1 | 60.7 ± 5.1 | 60.2 ± 1.5 |
| 18:3 | 8.8 ± 2.0 | 1.9 ± 0.3 | 1.4 ± 0.2 |

[a]The percentage of lipid by fresh weight of tissue was 0.4 ± 0.1, 4.0 ± 1.1, and 3.9 ± 0.6 for embryogenic callus, somatic embryo, and zygotic embryo, respectively.
[b]Somatic embryos were grown on MS medium containing 6% sucrose and 10 mM ABA.
[c]Zygotic embryos were tested 12 DAP.

TABLE 5

Fatty acid composition of somatic embryos produced from transgenic cultures containing pDAB463.

| Culture Line | Average Fatty Acid Content Percent of Total Fatty Acids (±SE) | | | | | | Fatty Acid Content (% of fresh weight) |
|---|---|---|---|---|---|---|---|
| | 16:0 | 16:1 | 18:0 | 18:1 | 18:2 | 18:3 | |
| 463-09 | 13 | 0.4 | 0.5 | 16.7 | 67.7 | 1.5 | 4.7 |
| | ± | ± | ± | ± | ± | ± | ± |
| | 0.9 | 0.2 | 0.2 | 1.9 | 2.2 | 0.3 | 0.7 |
| Control | 12.5 | 0.0 | 1.3 | 18.2 | 65.8 | 1.5 | 4.9 |
| | ± | ± | ± | ± | ± | ± | ± |
| | 0.6 | 0.0 | 0.4 | 4.5 | 4.5 | 0.2 | 0.6 |
| 463-43 | 12.7 | 1.2 | 0.3 | 19.7 | 64.3 | 1.6 | 4.7 |
| | ± | ± | ± | ± | ± | ± | ± |
| | 0.7 | 0.3 | 0.1 | 3.1 | 3.3 | 0.5 | 1.2 |
| Control | 13.8 | 0.0 | 1.0 | 17.2 | 65.8 | 1.5 | 5.5 |
| | ± | ± | ± | ± | ± | ± | ± |
| | 0.7 | 0.0 | 0.2 | 2.4 | 2.7 | 0.3 | 1.3 |

Embryogenic callus from lines 463-09 and 463-43 was used to regenerate plants as described herein. The fatty acid methyl ester analysis procedure, as described herein, was performed on leaf tissue from these plants. Table 6 shows the total fatty acid composition of leaf tissue from lines 463-09 and 463-43, in which 16:1Δ9 averaged about 4.8% and about 5.5% respectively. These levels of 16:1Δ9 represent about a 3-fold or greater increase over that normally found in control leaves. The 16:0 level was reduced by 20% compared to the control in line 463-43.

Pollinations were made with plants from lines 463-09 and 463-43, seed were obtained as described herein, and fatty acid methyl ester analysis was performed on a small portion (0.5 to 1.5 mg) of each seed embryo. The average fatty acid composition of seed which contained 16:1Δ9 is shown in Table 7. The 16:1Δ9 content of lines 463-09 and 463-43 both averaged from about 0.7% to about 1.1%. The 18:0 content of both lines was reduced by approximately 50%. The data described herein demonstrate that an increased production of 16:1Δ9 in somatic embryos, leaves and seeds of maize, can be obtained by transformation with a gene construct composed of an Aspergillus palmitoyl-CoA Δ9 desaturase gene driven by a ubiquitin promoter.

TABLE 6

Fatty acid composition of leaves from plants produced from transgenic cultures containing pDAB463.

| Plant Line | Average Fatty Acid Content Percent of Total Fatty Acids (±SE) | | | | | | Fatty Acid Content (% of Fresh weight) |
|---|---|---|---|---|---|---|---|
| | 16:0 | 16:1 | 18:0 | 18:1 | 18:2 | 18:3 | |
| 463-09 | 19.2 | 4.8 | 0.7 | 1.6 | 17.0 | 45.2 | 0.5 |
| | ± | ± | ± | ± | ± | ± | ± |
| | 1.8 | 0.3 | 0.1 | 0.8 | 2.0 | 5.1 | 0.0 |
| 463-43 | 14.6 | 5.5 | 0.4 | 2.0 | 17.8 | 50.6 | 0.7 |
| | ± | ± | ± | ± | ± | ± | ± |
| | 2.1 | 0.7 | 0.1 | 0.8 | 3.8 | 6.2 | 0.2 |
| Control | 18.3 | 1.6 | 2.0 | 1.5 | 17.8 | 48.1 | 0.8 |
| | ± | ± | ± | ± | ± | ± | ± |
| | 1.7 | 0.7 | 0.7 | 0.5 | 2.9 | 7.2 | 0.2 |

TABLE 7

The fatty acid composition of seed embroys from 463-09 and 463-43.

| Plant Line | Average Fatty Acid Content Percent of Total Fatty Acids (±SE) | | | | | | Fatty Acid Content (% of fresh weight) |
|---|---|---|---|---|---|---|---|
| | 16:0 | 16:1 | 18:0 | 18:1 | 18:2 | 18:3 | |
| 463-09 | 15.1 | 0.7 | 0.8 | 23.6 | 58.1 | 1.1 | 21.1 |
| | ± | ± | ± | ± | ± | ± | ± |
| | 1.2 | 0.2 | 0.2 | 2.6 | 2.7 | 0.3 | 5.5 |
| 463-43 | 15.3 | 0.7 | 0.7 | 26.1 | 56.1 | 0.7 | 34.8 |
| | ± | ± | ± | ± | ± | ± | ± |
| | 0.9 | 0.1 | 0.0 | 1.1 | 0.6 | 0.3 | 8.3 |
| Control | 13.7 | 0.0 | 1.8 | 26.5 | 56.5 | 0.7 | 46.7 |
| | ± | ± | ± | ± | ± | ± | ± |
| | 0.5 | 0.0 | 0.2 | 1.2 | 1.0 | 0.1 | 5.4 |

Fatty acid methyl ester analysis of embryogenic callus transformed with pDAB470 showed that 16:1Δ9 was detected in somatic embryos and reached levels of about 1.8%. Detection of 16:1Δ9 was rare in the control lines, and when it was detected, the levels were never higher than about 0.2% in a single embryo. Table 8 shows the total fatty acid composition of somatic embryos produced from lines 470-10 and 470-12, in which 16:1Δ9 averaged about 0.5% and about 0.4% respectively.

Embryogenic callus from lines 470-10 and 470-12 was used to regenerate plants as described herein. The fatty acid methyl ester analysis procedure, as described herein, was performed on leaf tissue from these plants. The 16:1Δ9 levels in leaves from these plants were normal, as would be expected because of lack of expression of the embryo-specific promoter in leaf tissue. Pollinations were made with plants from lines 470-10 and 463-43, seed were obtained as described herein, and fatty acid methyl ester analysis was performed on a small portion (0.5 to 1.5 mg) of each seed embryo.

TABLE 8

Fatty acid composition of somatic embryos produced from transgenic cultures containing pDAB470.

| Culture Line | Average Fatty Acid Content Percent of Total Fatty Acids (±SE) | | | | | | Fatty Acid Content (% Of Total) |
|---|---|---|---|---|---|---|---|
| | 16:0 | 16:1 | 18:0 | 18:1 | 18:2 | 18:3 | |
| 470-10 | 12.6 | 0.5 | 0.5 | 17.3 | 67.1 | 1.5 | 5.4 |
| | ± | ± | ± | ± | ± | ± | ± |
| | 1.1 | 0.1 | 0.1 | 2.4 | 3.2 | 0.4 | 1.3 |
| 470-12 | 11.0 | 0.4 | 0.7 | 17.1 | 68.8 | 1.3 | 5.8 |
| | ± | ± | ± | ± | ± | ± | ± |
| | 0.8 | 0.3 | 0.2 | 2.4 | 2.3 | 0.3 | 0.8 |
| Control | 11.9 | 0.0 | 0.9 | 15.3 | 70.4 | 1.2 | 5.0 |
| | ± | ± | ± | ± | ± | ± | ± |
| | 0.5 | 0.0 | 0.2 | 2.0 | 2.1 | 0.2 | 0.9 |

The average fatty acid composition of seed which contained 16:1Δ9 is shown in Table 9. The 16:1Δ9 content of lines 470-10 and 470-12 averaged about 0.9% and about 1.7% respectively. The 18:0 content of both lines was reduced by more than about 50%. The 16:1Δ9 content observed in some seed embryo lines was about 3.2%. A reduction in 16:0 content of about 6% and a reduction in total saturated fatty acids of about 10% was observed in both lines. The data described herein demonstrate that an increased production of 16:1Δ9 and a concomitant decrease in 16:0 and total saturated fatty acids in seeds of maize, can be obtained by transformation with a gene construct composed of an Aspergillus Δ9 gene driven by an embryo-specific globulin promoter.

TABLE 9

The fatty acid composition of seed embryos from 470-10 and 470-12.

| Plant Line | Average Fatty Acid Content Percent of Total Fatty Acids (±SE) | | | | | | Fatty Acid Content (% of Fresh Weight) |
|---|---|---|---|---|---|---|---|
| | 16:0 | 16:1 | 18:0 | 18:1 | 18:2 | 18:3 | |
| 470-10 | 10.9 | 0.9 | 0.5 | 18.6 | 68.6 | 0.4 | 25.7 |
| | ± | ± | ± | ± | ± | ± | ± |
| | 0.6 | 0.4 | 0.1 | 1.1 | 1.3 | 0.1 | 8.9 |
| 470-12 | 10.6 | 1.7 | 0.4 | 19.1 | 67.1 | 0.4 | 27.9 |
| | ± | ± | ± | ± | ± | ± | ± |
| | 0.4 | 0.4 | 0.1 | 1.2 | 1.4 | 0.1 | 6.6 |
| Control | 11.9 | 0.0 | 1.4 | 16.3 | 69.3 | 0.7 | 30.0 |
| | ± | ± | ± | ± | ± | ± | ± |
| | 0.8 | 0.0 | 0.2 | 1.4 | 1.21 | 0.1 | 4.5 |

EXAMPLE 8

Identification of 16:1Δ9 in an Extract from a Seed Embryo Transformed with Aspergillus Δ-9 Desaturase Fatty acid methyl esters were extracted from a seed embryo produced from line 470-12 as described herein. The 16:1Δ9 methyl ester in the extract was identified by comparison of retention time to that of a standard 16:1Δ9 (Matreya, Pleasant Gap, Pa.). For a typical GC run, the standard 16:1Δ9 and the suspected 16:1Δ9 from the seed embryo extract both had retention times of about 4.3 min.

Further confirmation of 16:1 production involved identification of the suspected 16:1Δ9 peak by gas chromatography-mass spectrometry (GC-MS) and electron impact ionization using a DB-WAX capillary column (J&W Scientific, Folsom, Calif.) on a Hewlett Packard (Wilmington, Del.) 5890 Series II gas chromatograph equipped with a Hewlett Packard 5972 mass selective detector. Initially, the standard 16:1Δ9 was examined to determine the mass spectral fragmentation pattern. This peak eluded at 14.12 minutes and had a mass spectrum with the molecular ion at m/z 268 and fragment ions at m/z 152, m/z 194 and m/z 236. to determine position of unsaturation, an iodine catalyzed dimethyl disulfide derivatization, after a published method (Yamamoto et. at., 1991 Chemistry and Physics of Lipids 60:39), was performed on the standard 16:1Δ9 for 1 h at 35° C. Following addition of hexane/ether and aqueous $Na_2S_2O_3$, the reaction products were analyzed directly by GC-MS. The resultant derivative eluded at 32.46 minutes. The mass spectrum of this derivatized standard had a molecular ion present at m/z 362 and major fragment ions occurring at m/z 145 and m/z 217. This cleavage pattern between the methylthio-substituted carbons was used to determine the double-bond position as being between the C9 and C10 position relative to the acid portion of the molecule in the 16:1Δ9 standard.

The extract from the 470-12 seed embryo was analyzed by GC-MS. This sample contained the suspected 16:1Δ9 peak at about 14.11 min with a fragmentation pattern consistent with the standard 16:1Δ9 methyl ester (molecular ion at m/z 268 and fragment ions at m/z 152, m/z 194 and m/z 236). After derivatization of this sample as described herein, the peak shifted from about 14.11 min to about 32.43 min.

The mass spectrum produced from the approximate 32.43 min peak was consistent with the derivatized standard (molecular ion present at m/z 362 and major fragment ions occurring at m/z 145 and m/z 217). These results indicated that the suspected 16:1Δ9 methyl ester in the 470-12 sample is indeed 16:1Δ9 and that the protein encoded by the gene disclosed herein is truly a palmitoyl-CoA Δ-9 desaturase.

EXAMPLE 9

Designing a Gene Encoding the Aspergillus Delta-9 Desaturase for High Level Expression in Maize A new DNA sequence is chemically synthesized in such fashion that the amino acid sequence of the protein encoded by the new DNA sequence is substantially the same, or identical, to the Aspergillus palmitoyl-CoA Δ-9 desaturase amino acid sequence as set forth in SEQ ID NO:6. As described herein, substitutions are made for the nucleotides of the native gene sequence in such a manner as to conserve the identity of the encoded amino acid. However, alterations in codon composition of the new DNA sequence are made such that the overall codon composition of the new DNA sequence more closely resembles the overall codon composition found in maize genes that encode proteins. Furthermore, the choice of said codons used to substitute for the native codons is preferably the most abundantly used maize codon, but choices can also be made amongst the less preferred maize codon choices to fulfill such desirable attributes as to increase the number of TG and CT base doublets, to decrease the numbers of CG and TA doublets, to remove intron splice sites, to remove polyadenylation signal sequences, to add or remove restriction enzyme recognition sequences, or to add or remove other sequences which may enhance or detract from, respectively, the overall expression level of the gene, as is understood by those skilled in the art. Such an example of a redesigned gene suitable for high level expression in maize plants is disclosed herein as SEQ ID NO:12. Except for the addition of a new alanine residue encoded by the second codon, the encoded protein of SEQ ID NO:12 is identical to the protein encoded by the native Aspergillus delta-9 desaturase gene as disclosed herein As can be seen by examination of Table 10, the native Aspergillus delta-9 desaturase gene has a codon composition substantially different from that employed by maize, particularly for the arginine CGT and AGG codons, the serine AGC codon, and the glutamine CAA codon. As is also disclosed in Table 10 the redesigned coding region disclosed as SEQ ID NO:12 employs a codon composition that reflects the average codon composition of maize genes that encode proteins, except that codons that are used less than 10% of time in maize genes are avoided. The redesigned gene has a content of G plus C residues of 56.8%, well within the range of other maize genes that encode proteins.

The gene created as described herein and having the SEQ ID NO:12 can then be cloned into the appropriate vector for expression. As described herein, the maize codon biased gene (SEQ ID NO:12) can be cloned into pBAD439 and inserted into maize plants as described herein to produce a plant whereby the gene is expressed in a constitutive manner. In addition, the gene can also be cloned 3' to the globulin promoter as described herein for pDAB470 to produce maize plants wherein the maize codon biased Aspergillus delta-9 gene is expressed in seed embryos.

TABLE 10

Aspergillus codon usage and Maize bias table for creating a maize optimized gene encoding for Aspergillus delta-9 desaturase.

| Codon | Amino Acid | Number in Native Gene | % Usage in Native Gene | Number in Rebuilt Gene | % Usage in Rebuilt Gene | Maize % Usage |
|---|---|---|---|---|---|---|
| TTT | Phe | 1 | 6.7 | 4 | 26.7 | 24 |
| TTC | Phe | 14 | 93.3 | 11 | 73.3 | 76 |
| TTA | Leu | 0 | 0 | 0 | 0 | 5 |
| TTG | Leu | 4 | 11.4 | 5 | 14.3 | 15 |
| TCT | Ser | 6 | 37.5 | 2 | 12.5 | 14 |
| TCC | Ser | 6 | 37.5 | 4 | 25.0 | 24 |
| TCA | Ser | 1 | 6.3 | 3 | 18.8 | 13 |
| TCG | Ser | 2 | 12.5 | 3 | 18.8 | 16 |
| TAT | Tyr | 3 | 15.8 | 4 | 21.1 | 20 |
| TAC | Tyr | 16 | 84.2 | 15 | 78.9 | 80 |
| TAA | Stop | 0 | 0 | 0 | 0 | 12 |
| TAG | Stop | 0 | 0 | 0 | 0 | 42 |
| TGT | Cys | 1 | 25.0 | 2 | 50.0 | 25 |
| TGC | Cys | 3 | 75.0 | 2 | 50.0 | 75 |
| TGA | Stop | 1 | 100 | 1 | 100 | 46 |
| TGG | Trp | 20 | 100 | 20 | 100 | 100 |
| CTT | Leu | 10 | 28.6 | 8 | 22.9 | 16 |
| CTC | Leu | 12 | 34.3 | 9 | 25.7 | 26 |
| CTA | Leu | 1 | 2.9 | 3 | 8.6 | 10 |
| CTG | Leu | 8 | 22.9 | 10 | 28.6 | 28 |
| CCT | Pro | 5 | 25.0 | 5 | 25.0 | 20 |
| CCC | Pro | 8 | 40.0 | 4 | 20.0 | 25 |
| CCA | Pro | 4 | 20.0 | 5 | 25.0 | 26 |
| CCG | Pro | 3 | 15.0 | 6 | 30.0 | 29 |
| CAT | His | 3 | 15.0 | 6 | 30.0 | 35 |
| CAC | His | 17 | 85.0 | 14 | 70.0 | 65 |
| CAA | Gln | 0 | 0 | 8 | 47.1 | 44 |
| CAG | Gln | 17 | 100 | 9 | 52.9 | 56 |
| CGT | Arg | 16 | 57.1 | 3 | 10.7 | 10 |
| CGC | Arg | 11 | 39.3 | 10 | 35.7 | 34 |
| CGA | Arg | 0 | 0 | 0 | 0 | 4 |
| CGG | Arg | 0 | 0 | 4 | 14.3 | 14 |
| ATT | Ile | 8 | 27.6 | 9 | 31.0 | 27 |
| ATC | Ile | 21 | 72.4 | 16 | 55.2 | 60 |
| ATA | Ile | 0 | 0.0 | 4 | 13.8 | 13 |
| ATG | Met | 9 | 100 | 9 | 100 | 100 |
| ACT | Thr | 5 | 23.8 | 4 | 19.0 | 18 |
| ACC | Thr | 11 | 52.4 | 9 | 42.9 | 45 |
| ACA | Thr | 2 | 9.5 | 3 | 14.3 | 15 |
| ACG | Thr | 3 | 14.3 | 5 | 23.8 | 22 |
| AAT | Asn | 0 | 0 | 4 | 23.5 | 21 |
| AAC | Asn | 17 | 100 | 13 | 76.5 | 79 |
| AAA | Lys | 3 | 12.5 | 5 | 20.8 | 19 |
| AAG | Lys | 21 | 87.5 | 19 | 79.2 | 81 |
| AGT | Ser | 0 | 0 | 0 | 0 | 7 |
| AGC | Ser | 1 | 6.3 | 4 | 25.0 | 26 |
| AGA | Arg | 0 | 0 | 0 | 0 | 8 |
| AGG | Arg | 1 | 3.6 | 11 | 39.3 | 30 |
| GTT | Val | 11 | 31.4 | 7 | 20.0 | 18 |
| GTC | Val | 16 | 45.7 | 11 | 31.4 | 33 |
| GTA | Val | 0 | 0 | 0 | 0 | 7 |
| GTG | Val | 8 | 22.9 | 17 | 48.6 | 42 |
| GCT | Ala | 12 | 28.6 | 11 | 25.6 | 26 |
| GCC | Ala | 21 | 50.0 | 16 | 37.2 | 33 |
| GCA | Ala | 3 | 7.1 | 6 | 14.0 | 15 |
| GCG | Ala | 6 | 14.3 | 10 | 23.3 | 26 |
| GAT | Asp | 8 | 28.6 | 11 | 39.3 | 32 |
| GAC | Asp | 20 | 71.4 | 17 | 60.7 | 68 |
| GAA | Glu | 5 | 31.3 | 4 | 25.0 | 24 |
| GAG | Glu | 11 | 68.8 | 12 | 75.0 | 76 |
| GGT | Gly | 22 | 55.0 | 10 | 25 | 21 |
| GGC | Gly | 13 | 32.5 | 17 | 42.5 | 45 |
| GGA | Gly | 3 | 7.5 | 5 | 12.5 | 13 |
| GGG | Gly | 2 | 5.0 | 8 | 20.0 | 21 |

We claim:

1. An isolated nucleic acid having a nucleotide sequence of SEQ ID NO:5 or SEQ ID NO:12.

2. An isolated nucleic acid encoding the protein of SEQ ID NO:6.

3. A DNA construct comprising, in the 5' to 3' direction: a promoter regulatory element, a nucleic acid fragment encoding a palmitoyl-CoA Δ-9 desaturase from Aspergillus, and a transcriptional terminator sequence, wherein either said promoter regulatory element or said transcription termination sequence is not naturally associated with said nucleic acid fragment.

4. The construct of claim 3 wherein said promoter regulatory element is selected from the group consisting of ubiquitin promoter, maize globulin promoter, maize streak virus leader sequence, 35s promoter, 35T promoter, the first intron of maize alcohol dehydrogenase and beta-phaseolin promoter.

5. The construct of claim 3 wherein said nucleic acid fragment is selected from the group consisting of SEQ ID NO:5 and SEQ ID NO:12.

6. A plant cell stably incorporating into its genome the nucleic acid construct of claim 3.

7. A plant cell stably incorporating 4 into its genome the nucleic acid construct of claim 5.

8. A plant cell of claim 6 wherein said promoter regulatory element is selected from the group consisting of ubiquitin promoter, maize globulin promoter, maize streak virus enhancer region, 35s promoter, doubly enhanced 35s promoter, the first intron of maize alcohol dehydrogenase and beta-phaseolin.

9. A plant cell of claim 6 wherein said plant cell is selected from the group consisting of soybean, a Brassicaceae species, canola, rape, sunflower, flax, safflower, coconut, palm, olive, peanut, cotton, castor bean, coriander, a Crambe species, a Cuphea species, a Euphorbia species, a Oenothera species, jojoba, a Lesquerella species, marigold, a Limnanthes species, a Vernonia species, Sinapis alba, cocoa, tobacco, and maize.

10. A plant cell of claim 6 wherein said cell is a seed embryo cell.

11. A transgenic plant produced from a plant cell of claim 6.

12. Seed and progeny thereof which stably incorporate the nucleic acid construct of claim 4, said seed and progeny produced from a transgenic plant of claim 11.

13. A method of producing a plant oil having altered levels of fatty acids comprising: growing a plant cell having integrated into its genome a construct comprising, in the 5' to 3' direction, a promoter regulatory element functional in a plant cell; a nucleic acid fragment that encodes a delta-9 CoA desaturase isolated from Aspergillus, the delta-9 CoA desaturase selected from the group consisting of SEQ ID NO:6, SEQ ID NO:6 with conservative amino acid substitutions, and derivatives of any thereof; and a transcriptional terminator sequence.

* * * * *